United States Patent [19]

Carson

[11] Patent Number: 4,742,084
[45] Date of Patent: * May 3, 1988

[54] ARALYKYL (ARYLETHYNYL)ARALKYL AMINES AND THEIR USE AS VASODILATORS AND ANTIHYPERTENSIVES

[75] Inventor: John R. Carson, Norristown, Pa.

[73] Assignee: McNeilab, Inc., Fort Washington, Pa.

[*] Notice: The portion of the term of this patent subsequent to Apr. 28, 2004 has been disclaimed.

[21] Appl. No.: 932,433

[22] Filed: Nov. 19, 1986

Related U.S. Application Data

[63] Continuation of Ser. No. 665,684, Oct. 29, 1984, Pat. No. 4,661,635, which is a continuation-in-part of Ser. No. 553,726, Nov. 21, 1987, abandoned.

[51] Int. Cl.$^4$ .................... C07C 87/28; A61K 31/135
[52] U.S. Cl. ...................................................... 514/654
[58] Field of Search .................. 564/374, 381, 282; 514/654, 643

[56] References Cited

U.S. PATENT DOCUMENTS 3,719,712 3/1973 Remy .................................. 564/374
4,661,635 3/1987 Carson ................................ 564/374

FOREIGN PATENT DOCUMENTS 813564 3/1981 South Africa.

OTHER PUBLICATIONS

"Antiarrhythmic Agents, 2-, 3- and 4-Substituted Benzylamines", David C. Remy, J. Med. Chem., 1975, vol. 18, No. 2, pp. 142–148.

Primary Examiner—Charles F. Warren
Assistant Examiner—John A. Sopp
Attorney, Agent, or Firm—David J. Levy

[57] ABSTRACT

Acetylenes of the formula (I):

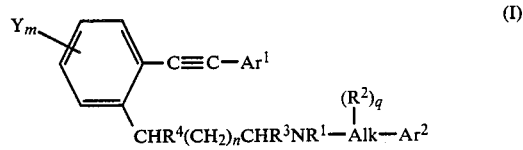

wherein Y, m, $R^1$, $R^2$, q, Alk, $R^3$ n and $R^4$ are as defined herein and $Ar^1$ and $Ar^2$ are aromatic, including the salts and ammonium derivatives of formula (I), in treating angina, hypertension and cardiac arrhythmias. Pharmaceutical compositions, methods of use and synthesis and novel intermediates are also part of the invention.

6 Claims, No Drawings

ARALYKYL (ARYLETHYNYL)ARALKYL AMINES AND THEIR USE AS VASODILATORS AND ANTIHYPERTENSIVES

This is a continuation of U.S. Ser. No. 665,684, filed Oct. 29, 1984, now U.S. Pat. No. 4,661,635, which was a continuation-in-part of U.S. Ser. No. 553,726, filed Nov. 21, 1987 now abandoned.

The present invention comprises various aromatic derivatives of amino acetylenes which are useful as vasodilators and in the treatment of hypertension, e.g. in humans.

Various phenylethynyl benzylamines are claimed in U.S. Pat. No. 3,719,712 and are taught as antiarrhythmic agents.

SUMMARY OF THE INVENTION

Aromatic amino acetylenes of the following formula (I):

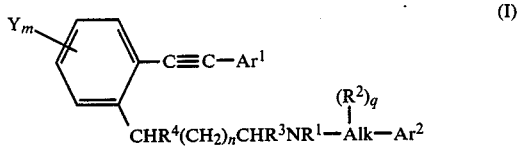

wherein Y, m, $R^1$, $R^2$, q, Alk, $R^3$, n and $R^4$ are as defined herein and $Ar^1$ and $Ar^2$ contain aromatic moieties have been found to possess vasodilating and anti-hypertensive properties when administered to a mammal in need thereof. Also part of the invention are pharmaceutical compositions containing compounds of the formula (I) and methods of treatment using such compositions.

DETAILED DESCRIPTION OF THE INVENTION

Compounds of the invention are of the following formula (I):

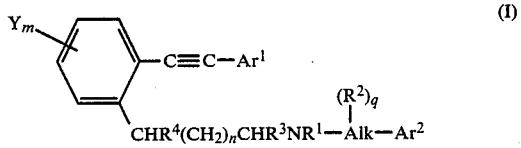

wherein

Y is independently alkyl, alkoxy, alkylthio, alkylsulfinyl, alkylsulfonyl, alkanoyloxy, alkanoylamino, amino, monoalkylamino, dialkylamino, hydroxy, halogen or cyano or methylenedioxy or ethylenedioxy at adjacent ring carbons;

m is 0, 1, 2 or 3;

$Ar^1$ is phenyl or a 5- or 6-membered heterocyclic aromatic ring which rings may be independently substituted by one or more of alkyl, alkoxy, alkylthio, alkylsulfinyl, alkylsulfonyl, amino, alkylamino, dialkylamino, carboxamido, halogen, fluoroalkyl or cyano;

$R^1$ is hydrogen, alkyl, hydroxyalkyl, cycloalkyl or cycloalkylalkyl or $R^1$ is independently selected from the group consisting of the defined values of —Alk— $Ar^2$;

$R^2$ is independently hydroxy, alkyl or phenyl;

Alk is a straight chain alkylene of about 1 to 4 carbons;

q is 0, 1 or 2 or 3 if Alk is alkylene of about 2 to 4 carbons;

$Ar^2$ is a phenyl, phenoxy, thiophenoxy, naphthyl or a 5- or 6-membered heterocyclic aromatic ring which rings may be substituted independently by one or more of alkyl, alkoxy, alkylthio, hydroxy, halogen, fluoroalkyl, nitro, amino or dialkylamino or by methylenedioxy at adjacent ring carbons;

$R^3$ is hydrogen, alkyl or alkoxyalkyl;

n is 0, 1 or 2; and $R^4$ is hydrogen or alkyl, provided that the hydroxy of the hydroxyalkyl for $R^1$ and the hydroxy for $R^2$ are not attached to the same carbon as the nitrogen atom in formula (I), and the pharmaceutically acceptable acid addition salts and quaternary ammonium compounds thereof.

In particular, Y is alkyl of about 1 to 6 carbons such as methyl or ethyl; alkoxy of about 1 to 6 carbon atoms such as methoxy or ethoxy; alkylthio of about 1 to 6 carbons such as methylthio; alkylsulfinyl of about 1 to 6 carbons such as methylsulfinyl; alkylsulfonyl of about 1 to 6 carbons such as methylsulfonyl; alkanoyloxy of about 2 to 6 carbons such as acetoxy; alkanoylamino of about 2 to 6 carbons such as acetylamino; amino; monoalkylamino of about 1 to 6 carbons such as ethylamino; dialkylamino of about 2 to 12 carbons such as dimethylamino; hydroxy; halogen such as fluoro, chloro or bromo; cyano; or methylenedioxy or ethylenedioxy wherein the two oxygen atoms are attached to two adjacent carbons of the benzene ring. Although the Y groups may be attached at any of the 4 open positions of the benzene ring, particularly preferred are compounds wherein the Y groups are attached at the 4- and/or 5-positions of the ring relative to the amino side chain with the acetylene moiety being at the 2-position.

$Ar^1$ is phenyl or a 5- or 6-membered heterocyclic aromatic ring containing 1, 2 or 3 heteroatoms such as nitrogen, sulphur or oxygen with specific examples being thiophene, pyrrole, furan, pyrazole, imidazole, triazole, oxazole, thiazole, thiadiazole, pyridine, pyridazine, pyrimidine, pyrazine or triazine. Such heterocycles may be attached via a ring carbon atom to the acetylene moiety. The optional substitution on the $Ar^1$ ring is one or more, same or different, of alkyl, alkoxy or alkylthio of about 1 to 6 carbons, such as methyl, ethyl, methoxy, iso-propoxy or methylthio; alkylsulfinyl or alkylsulfonyl of about 1 to 6 carbons such as methylsulfinyl; amino; alkylamino of about 1 to 6 carbons such as methylamino or isopropylamino; dialkylamino of about 2 to 12 carbons, e.g., of about 1 to 6 carbons in each alkyl group, such as dimethylamino or N-ethyl-N-n-propylamino; carboxamido of the formula —CONH$_2$; halogen such as fluoro, chloro, or bromo; fluoroalkyl of about 1 to 6 carbons and one or more fluoro atoms with examples being 2,2,2-trifluoroethyl and trifluoromethyl; or cyano. Such optional substituents may be attached at any available site on the phenyl or heterocyclic ring, in particular at the meta and para positions of a phenyl ring relative to the acetylene.

$R^1$ is hydrogen; alkyl of about 1 to 6 carbons such as methyl, ethyl or iso-propyl; hydroxyalkyl of about 1 to 6 carbons such as 2-hydroxyethyl; cycloalkyl of about 3 to 6 carbons such as cyclopropyl or cyclohexyl; or cycloalkylalkyl of about 4 to 7 carbons such as cyclopropylmethyl or $R^1$ is independently, i.e., independent of the value for —Alk—$Ar^2$ chosen for these symbols in formula (I), selected from the group consisting of the defined values of —Alk—$Ar^2$, i.e., the entire list of possible —Alk— values and —Ar$^2$ values. For example, R$^1$ can be phenethyl, i.e., R$^1$ is —Alk—Ar$^2$ where Alk is ethylene and Ar$^2$ is phenyl.

R$^2$ is independently hydroxy; alkyl of about 1 to 4 carbons such as methyl, ethyl or iso-propyl; or phenyl.

Alk is methylene, ethylene, trimethylene or tetramethylene.

q is 0, 1, 2 or 3, in particular 0, 1 or 2.

Ar$^2$ is phenyl; phenoxy; thiophenoxy; naphthyl, e.g., 1- or 2-naphthyl; or a 5- or 6-membered heterocyclic aromatic ring, preferably one having 1 heteroatom such as nitrogen, sulfur or oxygen, e.g. furan or thiophene attached at the 2 or 3 position, pyrrole attached at the 1, 2 or 3 position and pyridine attached at the 2, 3 or 4 position. The open positions of the ring, or rings in the case of naphthyl, of Ar$^2$ may be substituted by one or more, e.g. one or two, same or different, of alkyl of about 1 to 6 carbons such as methyl or ethyl; alkoxy of about 1 to 6 carbons such as methoxy and ethoxy; alkylthio of about 1 to 6 carbons such as methylthio; hydroxy; halogen such as fluoro, chloro and bromo; fluoroalkyl of about 1 to 6 carbons and one or more fluorine atoms with examples being 2,2,2-trifluoroethyl and trifluoromethyl; nitro; amino; or dialkylamino of about 2 to 12 carbons such as dimethylamino; or methylenedioxy at adjacent ring carbons particularly if Ar$^2$ is phenyl, phenoxy or thiophenoxy, e.g., 3,4-methylenedioxyphenyl.

R$^3$ is hydrogen; alkyl of about 1 to 6 carbons such as methyl, ethyl, iso-propyl and n-pentyl; or alkoxyalkyl of about 1 to 6 carbons in each alkyl portion such as methoxymethyl, n-butoxymethyl and ethoxyethyl.

R$^4$ is in particular, hydrogen; or alkyl of about 1 to 6 carbons with examples being methyl, ethyl and n-butyl.

The pharmaceutically acceptable acid-addition salts of the compounds of formula (I) include those of a mineral or organic acid such as hydrochloric, hydrobromic, hydroiodic, sulfuric, phosphoric, fumaric, maleic, cyclohexylsulfamic, citric, lactic, methanesulfonic and similar acids. The term "independently" is used with respect to Y, Ar$^1$ substitution, R$^2$ and Ar$^2$ substitution to indicate that when more than one of such substitution is possible, e.g., when q and m are 2 or 3, such substitution may be different from each other, e.g., when q is 2, one such R$^2$ may be —OH and the other —CH$_3$.

The quaternary ammonium compounds of the compounds of formula (I) include those formed with an alkylhalide or sulfate of about 1 to 6 carbons, e.g., an alkyl bromide or iodide such as methyl iodide. The salts and ammonium compounds may be prepared by conventional techniques.

Compounds of Formula (I) and other compounds of the invention may exist in various isomeric forms, e.g., in view of the presence of an asymmetric carbon. It is understood that the present invention includes all such individual isomers and their racemates. Also within the scope of the invention are compounds of the invention in the form of hydrates and other solvate forms.

Particular compounds of the invention may be defined as those of formula (I) having one or more of the following definitions: Y is alkoxy, particularly methoxy; m is 0 or 1 and the Y group is at the 5 position of the ring with the aminoalkyl and the acetylene moieties at the 1 and 2 positions, respectively; Ar$^1$ is phenyl or phenyl substituted with a single substituent such as chloro; R$^1$ is hydrogen or alkyl such as methyl; R$^2$ is methyl; q is 0 or 1; Alk is methylene or ethylene; Ar$^2$ is phenyl or phenyl with one or two substituents such as alkoxy, e.g., methoxy, or chloro; R$^3$ is hydrogen or methyl; n is 0 or 1; and R$^4$ is hydrogen.

Preferred compounds are of the formula (I) wherein (i) Y is methoxy at the position para to the acetylene; m is 1; Ar$^1$ is phenyl; R$^1$ is methyl; q is 0; Alk is ethylene; Ar$^2$ is 3,4-dimethoxyphenyl; R$^3$ is methyl; n is 1; and R$^4$ is hydrogen; or (ii) Y is methoxy at the position para to the acetylene; m is 1; Ar$^1$ is phenyl; R$^1$ is methyl; q is 0; Alk is ethylene; Ar$^2$ is 3,4-dimethoxypheny; R$^3$ is hydrogen; n is 0; and R$^4$ is hydrogen; or (iii) Y is methoxy at the position para to the acetylene; m is 1; Ar$^1$ is phenyl; R$^1$ is hydrogen; q is 0; Alk is ethylene; Ar$^2$ is 3,4-dimethoxyphenyl; n is 0; and R$^4$ is hydrogen; or (iv) Y is methoxy at the position para to the acetylene; m is 1; Ar$^1$ is phenyl; R$^1$ is methyl; q is 0; Alk is ethylene; Ar$^2$ is 3,4-dimethoxyphenyl; R$^3$ is methyl; n is 0, and R$^4$ is hydrogen; or (v) Y is methoxy at the position para to the acetylene; m is 1; Ar$^1$ is phenyl; R$^1$ is hydrogen; q is 0; Alk is ethylene; Ar$^2$ is 3,4-dichlorophenyl; n is 0; and R$^4$ hydrogen; or (vi) Y is methoxy at the position para to the acetylene; m is 1; Ar$^2$ is phenyl; R$^1$ is methyl; q is 0; Alk is ethylene; Ar$^2$ is 3,4-dichlorophenyl; R$^3$ is hydrogen; n is 0; and R$^4$ is hydrogen.

Unless otherwise noted, "alkyl" in the present specification, e.g., as part of an alkoxy group, is indicative of a straight or branched chain group.

Compounds of formula (I) may be prepared according to the following Reaction Scheme I:

Reaction Scheme I

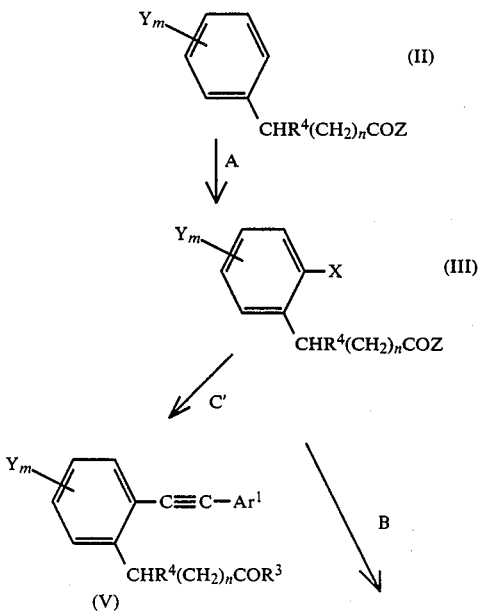

-continued
Reaction Scheme I

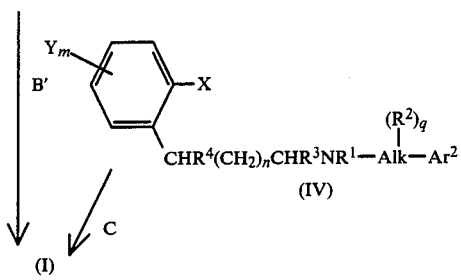

Three primary stages are used in the preparation of compounds of the formula (I) by starting with arylalkanoic acids or arylalkanones of the formula (II) wherein Z is OH or $R^3$, e.g., hydrogen, alkyl or alkoxyalkyl. The stages are halogenation, construction of an amine functionality and condensation with an $Ar^1$-acetylene. In the halogenation stage A, wherein X is a halogen such as Br or I, the aryl ring of (II) is halogenated in the position ortho to the eventual aminoalkyl side chain. Brominations may be carried out with bromine in halocarbon solvents or acetic acid at temperatures from about $-20°$ to 80° C. and may be conducted in the presence of a Lewis acid catalyst such as ferric chloride. Iodinations may be carried out using ICl or $INO_3$ in halocarbon solvents or acetic acid over a range of room temperature to about 100° C. Iodinations may be carried out using iodine in the presence of an iodide scavenger such as silver acetate, silver sulfate, mercuric oxide or nitric acid. For reactive substrates, iodine may be used alone or in conjunction with a mild base such as sodium bicarbonate. Alternatively, the halogenation may be accomplished by mercuration, e.g., with $HgCl_2$ or thallation, e.g., with $Tl(O_2CCF_3)_3$, followed by treatment with iodide or bromide as described by A. McKillop, et al. in J. Am. Chem. Soc., 93, 4841 (1971).

In stage B or B' the desired amine function is constructed. In a first embodiment for Stage B and if $R^3$ is to be hydrogen, a compound of formula (III) wherein Z is OH may be converted to the corresponding acid chloride by reagents such as oxalyl chloride, thionyl chloride or phosphoryl chloride. The reaction may be carried out at room temperature to about 100° C. in an aprotic, nonpolar solvent such as toluene, chloroform or methylene chloride or the reaction may be carried out neat. The preferred method employs oxalyl chloride in toluene in the presence of DMF. The acid chloride is converted to the corresponding amide of formula (III) wherein Z is $NR^1$—$Alk(R^2)_q$—$Ar^2$. This conversion may be carried out by treatment of the acid chloride with an excess of amine of the formula $R^1NH$—$Alk(R^2)_qAr^2$, for instance in toluene or a halocarbon solvent at temperatures from $-30°$ C. to 45° C. Alternatively, slightly more than one equivalent of amine may be used in the presence of an auxillary base such as triethylamine, pyridine, sodium hydroxide or potassium carbonate. The amide is then reduced to the corresponding amine of the formula (IV) wherein $R^3$ is hydrogen to complete elaboration of the amine function. The reduction of the amide is preferably carried out with an excess of borane in THF at the reflux temperature of the solvent. The excess borane is decomposed by addition of water and the amine borane complex is decomposed by heating in the presence of an alkanoic acid, preferably propionic acid, a mineral acid or an alkali metal hydroxide to give the amine of formula (IV) wherein $R^1$ is hydrogen. Alternatively, the amide may be reduced with lithium aluminum hydride, sodium borohydride plus aluminum chloride or sodium borohydride in acetic or trifluoroacetic acid. A second embodiment for the construction of the amine function consists of reductive alkylation of amines of the formula $R^1NH$—$Alk(R^2)_q$—$Ar^2$ by aldehydes or ketones of the formulae (III) or (V) wherein Z is $R^3$, i.e., hydrogen, alkyl or alkoxyalkyl. The reductive alkylation may be carried out in one step from the carbonyl compound and the amine using sodium cyanoborohydride as the reducing agent in a lower alkanol or acetonitrile as the solvent at neutral to mildly acidic pH at temperatures from 0° to 40° C. Hydrogenation over a noble metal catalyst may also be used to bring about the reduction. Reductive alkylation may also be carried out in two steps. The carbonyl compound and amine are first converted to an imine or iminium salt by treatment with molecular sieves or azeotropic removal of water. Reduction is then effected by $NaBH_4$, $NaCNBH_3$ or catalytic reduction. Using the two step reductive alkylation, the alkyl groups $R^1$ and —$Alk(R^2)_q$—$Ar^2$ may be attached sequentially. In stage B', the reductive alkylation cannot be carried out by catalytic hydrogenation in view of the possibility of hydrogenation of the acetylene moiety.

If $R^1$ is to be methyl, the Eschweiler-Clark procedure using formaldehyde as the carbonyl compound and formic acid or sodium cyanoborohydride as the reducing agent is used.

The third stage in Reaction Scheme I is the replacement of halide X by an $Ar^1$-acetylene and is labeled C and C'. For stage C, the transformation may be carried out by heating the aryl halide (IV) with a cuprous $Ar^1$-acetylide at the reflux temperature of the solvent, preferably pyridine or DMF as described by R. D. Stephens, et al. in J. Org. Chem., 28, 3313 (1963). Secondly, the coupling of the arylhalides (III) or (IV) with an $Ar^1$-acetylene may be accomplished by treating the arylhalide with chlorozinc $Ar^1$-acetylide in the presence of a palladium or nickel catalyst, preferably $Pd[(Ph_3)P]_4$ in an etherial solvent such as THF at $-30°$ C. to ambient temperature, as described by A. O. King et al. in J. Org. Chem., 43, 358 (1978). Thirdly, coupling may be by treating the arylhalide (III) or (IV) with the $Ar^1$-acetylene and catalytic quantities, e.g., 0.5 to 10 mole percent, of $Pd[(Ph_3)P]_4$, $Pd(OAc)_2$ $[P(Ph)_3]_2$ or $PdCl_2[P(Ph)_3]_2$ in an amine solvent such as diethylamine, piperidine, pyrrolidine or triethylamine at ambient temperature to the reflux temperature of the solvent in the presence or absence of cuprous iodide as described by K. Sonogashira et al. in Tetrahedron Letters, 4467 (1975) or H. A. Dieck et al. in J. Organometal. Chem. 93, 253 (1975). When $R^1$ is to be hydrogen, the method of Stephens et al. may not be used. The stages of reaction Scheme I may be carried out in the sequence A, B and C or the sequence A, C' and B'. Uhen $R^1$ is to be alkyl, such may be attached by reductive alkylation after carrying out stage C or B'.

A second general method for preparation of compounds of formula (I) where n is 0, $R^4$ is H and $R^3$ is alkyl is shown in Reaction Scheme II:

Reaction Scheme II

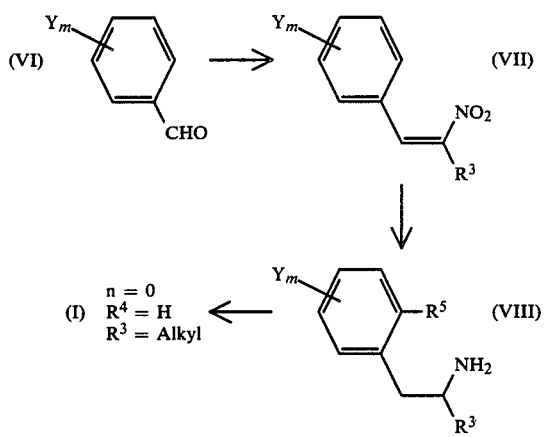

An aromatic aldehyde (VI) is condensed with a nitroalkane of the formula $R^3CH_2NO_2$ to afford a nitroolefin (VII). Condensation of the nitroalkane with the aromatic aldehyde is carried out using ammonium acetate or a primary alkylamine as catalyst in, for example, glacial acetic acid, ethanol or toluene as the solvent at ambient to elevated temperatures preferably at the reflux temperature of the solvent. The nitroolefin (VII) is then reduced to an amine (VIII) where $R^5$ is hydrogen with lithium aluminum hydride in an ether solvent, or by catalytic reduction over Raney nickel or a noble metal catalyst. The amine (VIII) is halogenated on the aromatic ring using the methods described for Stage A to afford a halogenated amine of the formula (VIII) where $R^5$ is halo. The haloamine is coupled with an $Ar^1$-acetylene using the procedure of King et al. or Sonogashiri et al. as described for Stage C to give an acetylene of formula (VIII) where $R^5$ is $-C\equiv C-Ar^1$. Attachment of the groups $-Alk(R^2)_q-Ar^2$ and/or $R^1$ by reductive alkylation starting with the appropriate carbonyl compounds, e.g., $CH_3CHO$ to have ethyl as the $R^1$ moiety or benzaldehyde to give benzyl as the $-Alk(R^2)_q-Ar^2$ moiety, affords the product of the formula (I) wherein n is 0, $R^4$ is hydrogen and $R^3$ is alkyl.

Starting materials for Reaction Schemes I and II are widely known. However, starting materials with particular substituents may be synthesized by the following methods:

First, alkanones of the formula (II) wherein Z is $R^3$, n is 0 and $R^4$ is hydrogen may be prepared by condensation of an aromatic aldehyde (VI) with an alpha-haloester, e.g. of the formula $R^3CHBrCOOAlkyl$ in the presence of an alkali metal alkoxide to give a glycidic ester of the formula (IX). Hydrolysis with an alkali metal hydroxide followed by thermal decarboxylation affords the arylalkanone (II) wherein Z is $R^1$, n is 0 and $R^4$ is hydrogen. Conversion of such a (II) compound to one wherein $R^1$ is alkyl may be carried out by alkylation of an alkali metal enolate of the carbonyl compound (II) with a reagent such as ethyl iodide.

Second, arylalkanones of the formula (II) where Z is $R^3$, n is 1 and $R^4$ is hydrogen may be prepared by a Claisen-Schmidt condensation of a methyl ketone, $CH_3COR^3$ with an aromatic aldehyde (VI) in the presence of an alkali metal hydroxide followed by hydrogenation of the alpha,beta-unsaturated ketone (X) over a noble metal catalyst. Third, arylalkanoic acids of the formula (II) wherein Z is OH, $R^4$ is hydrogen and n is 1 may be prepared by Knoevenagel condensation of an aromatic aldehyde (VI) with malonic acid followed by hydrogenation of the resulting cinnamic acid (XI) over a noble metal catalyst:

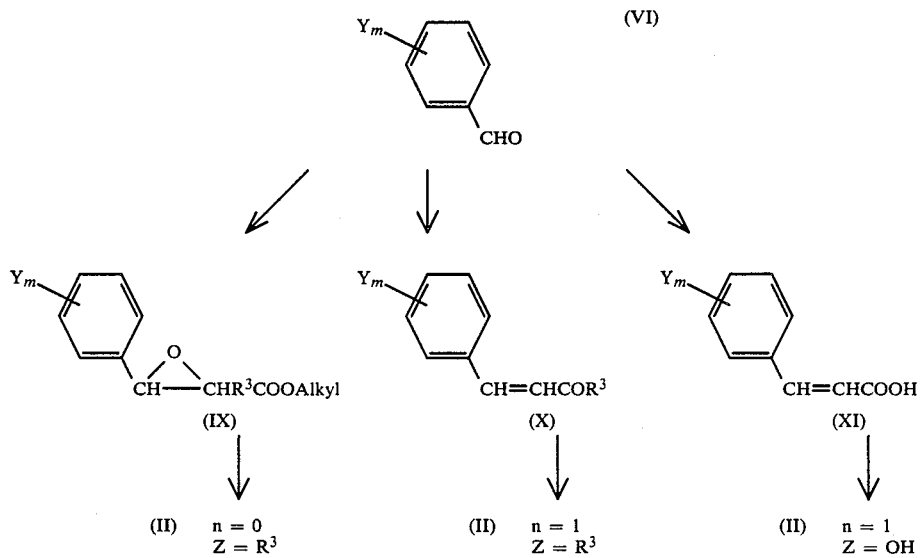

In each of the above three sequences, the aromatic aldehyde may be one with an X group ortho to the CHO and such a starting material will result in final products of the formula (III) after the steps described above.

For the preparation of intermediates (II) and (III) where Y is halo, alkylthio, hydroxy, cyano or dialkylamino, the corresponding compounds (XII) where p is 0 or 1, respectively, may be utilized as starting materials. The amine (XII) may be diazotized to give (XIII) and the diazonium group may be treated with CuCl, CuBr or CuCN to yield (II) or (III) wherein Y is Cl, Br or CN, respectively. Pyrolysis of the diazonium fluoroborate or hexafluoro phosphate gives the corresponding aryl fluoride. Hydrolysis of the diazonium salt would lead to the corresponding phenol. Treatment of the diazonium salt successively with potassium ethyl xanthate, base and an alkyl halide leads to the alkylthio product. Reductive alkylation of the amino compound (XII) with formaldehyde or an alkanal and sodium cyanoborohydride gives rise to intermediates (II) or (III) bearing the dialkylamino group.

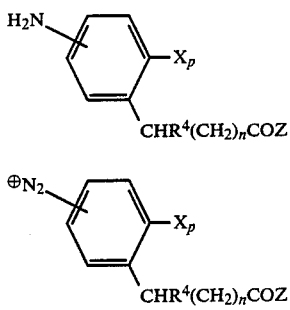

The various Y groups in compounds such as those of formulae (II), (III), (IV) and (XII) may be transformed among each other by techniques known in the art. For example, when Y is amino, the corresponding compound wherein Y is monoalkylamino may be prepared by acylation with an acyl halide or anhydride to yield the corresponding compound where Y is alkanoylamino followed by hydride reduction with borane or lithium aluminum hydride. When Y is alkylthio the corresponding comoound where Y is alkylsulfinyl or alkylsulfonyl may be produced by oxidation with hydrogen peroxide or a peracid such as trifluoroperacetic acid known in the art. Variation in the reaction temperature, reaction time and reactivity of the substrate and particular reagent will all be factors influencing whether the product is the sulfinyl or sulfonyl and manipulation of such variables is well known in the art. When Y is alkoxy, the corresponding compound wherein Y is hydroxy may be produced by conventional dealkylating reagents such as boron tribromide, boron trichloride, trimethylsilyliodide and hydrogen iodide. In addition, compounds wherein Y is alkoxy may be produced from the phenol by alkylation with a reagent such as alkyl halide, e.g., methyl iodide, in the presence of a base.

$Ar^1$-acetylenes as required may be prepared by the method of Ames et al as described in Synthesis, 364 (1981). Treatment of $Ar^1$ iodides of the formula $Ar^1$—I with $PdCl_2[(Ph)_3P]_2$ or $Pd(OAc)_2[(Ph)_3P]_2$ and 2-methyl-3-butyn-2-ol affords acetylenic carbinols (XIV). Cleaveage of the carbinol (XIV) with an alkali metal hydroxide gives rise to the $Ar^1$-acetylenes. The $Ar^1$-acetylenes may be converted to cuprous $Ar^1$-acetylides by treatment with cuprous iodide in ammonium hydroxide solution.

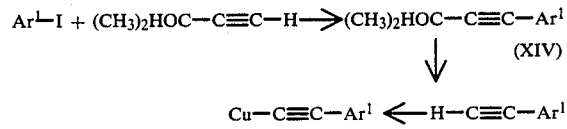

Compounds of the formula (I), including the acid-addition salts and quaternary compounds thereof, are calcium blockers and as such, are effective against angina, hypertension and cardiac arrhythmias in mammals, particularly as described by S. F. Flaim et al. in "Calcium Blockers Mechanisms of Action and Clinical Applications", Urban and Schwarzenberg, Baltimore, Md. (1982). Techniques used to determine efficacy as a calciium blocker are described by S. F. Flaim et al. in Pharmacology, Vol. 22, p. 286 to 293 (1981). Compounds of the invention have the advantage of a significant separation between the desirable coronary vasodilator effects and the less desirable side effect of decreased myocardial contractile force.

The activity of compounds of formula (I) for the treatment of hypertension was determined using the Spontaneously Hypertensive Rat (SHR) test as described below.

In this test, the arterial pressure of adult spontaneously hypertensive rats (Charles River) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hours. A test compound is considered to be active as an antihypertensive agent if the mean arterial pressure (MAP) indicates a fall of >15 mm of Hg. Each animal serves as its own control.

The results of this test for compounds of formula (I), expressed as "Max Fall BP" (Maximum Fall in Mean Arterial Pressure) are shown in Table I.

In addition to their utility in the treatment of hypertension, the compounds of formula (I) are useful in the treatent of the symptoms of angina pectoris by virtue of their ability to dilate coronary arteries. Their activity was measured using the "Langendorff's isolated heart" preparation. This test has been described in "Pharmacological Experiments on Isolated Preparations", Staff of the Department of Pharmacology, University of Edinbourgh, 2nd Ed., Churchill Livingstone, N.Y., 1970, pp. 112-119. The test compounds were adminsistered at concentrations of 3000, 1000, 300, 100, 30, 10, 3, 1 and 0.3 nanomolar ($10^{-9}$ molar).

The minimum concentration ($EC_{30}$) needed to elicit a 30 percent increase in coronary flow is shown in Table I for compounds of the formula (I) wherein Y is methoxy at the position para to the acetylene; m is 1; n is O except in the results for Example 32 where n is 1; $Ar^1$ is phenyl; q is O; Alk is ethylene; and $R^4$ is hydrogen.

TABLE I

| Example Number[a] | $R^1$ | $R^3$ | $Ar^2$ | Max Fall BP[b] (dose[c]) | $EC_{30}$ ($\times 10^{-9}$ M) |
|---|---|---|---|---|---|
| 32 | $CH_3$ | $CH_3$ | $3,4-(CH_3O)_2C_6H_3$ | 40 (30) | 30 |
| 39 | $CH_3$ | H | $3,4-(CH_3O)_2C_6H_3$ | 70 (30) | 10 |
| 33 | H | $CH_3$ | $3,4-(CH_3O)_2C_6H_3$ | 67 (30) | 10 |
| 40 | $CH_3$ | $CH_3$ | $3,4-(CH_3O)_2C_6H_3$ | 77 (3) | 10 |
| 33 | H | $CH_3$ | $3,4-Cl_2C_6H_3$ | ˙43 (3) | 0.1 |

TABLE I-continued

| Example Number[a] | R[1] | R[3] | Ar[2] | Max Fall BP[b] (dose[c]) | EC$_{30}$ (× $10^{-9}$ M) |
|---|---|---|---|---|---|
| 40 | CH$_3$ | CH$_3$ | 3,4-Cl$_2$C$_6$H$_3$ | 84 (3) | 0.3 |

[a] All test results were for the fumarate salt except Example 32 which was the hydrochloride
[b] in mm of Hg
[c] in mg/kg of body weight For the treatment of hypertension or angina, compounds of the present invention of the formula (I) may be administered orally or parenterally in a pharmaceutical composition comprising about 1 to 2,000 mg, preferably about 30 to 200 mg of one or more of the acetylene compounds per day for an average adult human depending on the activity of the particular compound chosen. The dosage may be divided into 1 to 4 unit dosage forms per day. While the therapeutic methods of the invention are most useful for human subjects in need of alleviation of hypertension or angina, the compounds may be administered to other mammals at comparable dosages per weight of the subject.

Pharmaceutical compositions containing the acetylene compounds of the present invention of formula (I), an acid addition salt thereof or a quaternary ammonium compound thereof as the active ingredient may be prepared by intimately mixing the acetylene compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof.

Also part of the present invention are novel intermediates, e.g., of the formula (II).

In the following Examples, the following abbreviations are used: E (trans); Z (cis); bp (boiling point); mp (melting point); g (grams); ml (milliliters); glc (gas liquid chromatography); NMR (nuclear magnetic resonance); J (coupling constant); d (doublet); dd (double doublet); s M(singlet); m (multiplet); t (triplet); N (normal); (molar); THF (tetrahydrofuran); MeOH (methanol); DMF (dimethylforamide); mmoles (millimoles); mg (milligrams); mm (millimeters); hr (hours); min (minutes); and C,H,N, etc. (the chemical symbols for the elements). Unless otherwise indicated, all temperatures are reported in degrees centigrade (°C.), all pressures in mm of mercury and all references to ether are to diethyl ether.

EXAMPLE 1

2-Iodo-5-methoxybenzeneacetic Acid

A solution of 45 g (0.27 mole) of 3-methoxybenzeneacetic acid, 52.6 g (0.32 mole) of iodine monochloride and 1 g of iodine was allowed to stand in 500 ml of glacial acetic acid for six days at room temperature. The reaction was poured into water and the solid collected. It was recrystallized from toluene to give 51 g of crystalline 2-iodo-5-methoxybenzeneacetic acid, mp 133.5°–134.5° C. (65% yield).

EXAMPLE 2

2-Iodo-5-methoxybenzenepropanoic Acid

Samples of iodine (138.6 g, 0.759 mole) and silver acetate (126.7 g, 0.759 mole) were added in portions over 20 min to a solution of 138.6 g (0.759 mole) of 3-methoxybenzenepropanoic acid in 750 ml glacial acetic acid. An additional 250 ml of glacial acetic acid was added. The mixture became warm and was stirred for one hour. The precipitated silver iodide was filtered and washed with acetic acid and the filtrate was poured into ice water and the solid collected. The solid was taken up in ether, washed with sodium thiosulfate solution and brine, dried with MgSO$_4$ and the solvent evaporated in vacuo. The residue was recrystallized from CHCl$_3$/ligroin to give 148.7 (64% yield) of 2-iodo-5-methoxybenzenepropanoic acid, mp 105°–106° C.

EXAMPLE 3

2-Iodo-5-methoxy-α-methylbenzeneethaneamine hydrochloride

Samples of iodine (49.7 g, 0.196 mole) and silver acetate (32.7 g, 0.196 mole) were added in portions to a solution of 29.4 g (0.178 mole) of 3-methoxy-α-methylbenzeneethanamine in 473 ml of glacial acetic acid. The mixture was stirred for one hour. The acetic acid was evaporated in vacuo. The residue was partitioned between ether and sodium hydroxide solution. The ether layer was washed with water and brine and dried with K$_2$CO$_3$. The solvent was evaported in vacuo to give 45.4 g of an oil. The hydrochloride was prepared from ethereal hydrogen chloride and recrystallized from CH$_3$CN to give 35.7 g of 2-iodo-5-methoxy-α-methylbenzeneethanamine hydrochloride, mp 194°–196° C.

EXAMPLE 4

1-(2-Iodo-5-methoxyphenyl)butane-3-one

Samples of iodine (42.4 g, 0.167 mole) and silver acetate (27.87 g, 0.167 mole) were added in portions to a solution of 29.8 g (0.167 mole) of 1-(3-methoxyphenyl)-butane-3-one in 167 ml of glacial acetic acid. The mixture was stirred one hour. The silver iodide was removed by filtration and washed with acetic acid. The filtrate was partitioned between ether and water. The ether layer was washed with water, sodium bicarbonate solution and sodium thiosulfate solution. The ether solution was dried with MgSO$_4$ and evaporated to dryness in vacuo. There was obtained 41.8 g (82% yield) of oily 1-(2-iodo-5-methoxyphenyl)butane-3-one.

¹HNMR (CDCl₃): 7.5–7.8 (d, J=9, 1H); 6.75–6.9 (d, J=3, 1H); 6.3–6.65 (dd, J=3, 10, 1H); 3.7–4.0 (s, 3H); 2.5–3.1 (m, 4H); 2.2 (s, 3H).

EXAMPLE 5

Using the procedure of Example 4 and substituting the appropriate ketone for 1-(3-methoxyphenyl)butane-3-one the following products were obtained respectively:
(2-iodo-5-methoxyphenyl)-2-propanone, mp 57°–58°
1-(2-iodo-5-methoxyphenyl)octan-3-one

EXAMPLE 6

2-Iodo-5-methoxybenzenepropanoyl chloride

To a solution of 13.0 g (0.042 mole) of 2-iodo-5-methoxybenzenepropanoic acid and 4 ml of DMF in 80 ml of dry toluene at 0° C. was added 4.00 ml (0.046 mole) of oxalyl chloride over 15 min. The reaction was stirred overnight to give a solution 2-iodo-5-methoxybenzenepropanoyl chloride in toluene.

EXAMPLE 7

By employing the appropriate starting materials and following the procedure of foregoing Example 6, the following intermediate acid chlorides were prepared:
2-Iodo-5-methoxybenzeneacetyl chloride
2-Iodo-5-methylthiobenzenepropanoyl chloride
5-Fluoro-2-iodobenzenepropanoyl chloride

EXAMPLE 8

N-[2-(3,4-Dimethoxyphenyl)ethyl]-2-iodo-5-methoxy-N-methylbenzenepropanamide

A solution of 13.8 g (0.042 mole) of 2-iodo-5-methoxybenzenepropanoyl chloride in 80 ml of toluene was cooled to 0° C. and 24.6 g (0.126 mole) of N-methylhomoveratrylamine was added over a 15-minute period. An additional 50 ml of toluene was added. The temperature was allowed to warm to room temperature and stirring continued for 3½ hours. The mixture was partitioned between 500 ml of methylene chloride and 400 ml of water. The methylene chloride layer was separated and washed with 400 ml of 5% hydrochloric acid followed by a washing with 400 ml of 5% sodium hydroxide solution. The organic phase was dried over anhydrous magnesium sulfate and evaporated in vacuo to yield N-[2-(3,4-dimethoxyphenyl)ethyl]-2-iodo-5-methoxy-N-methylbenzenepropanamide, a pale yellow oil that partially crystallized on standing.

EXAMPLE 9

Following the procedure of Example 8 and employing equivalent quantities of the appropriate acid chloride in place of 2-iodo-5-methoxybenzenepropanoyl chloride and the appropriate amine in place of N-methylhomoveratrylamine the following amides were obtained as products respectively:
N-[2-(3,4-Dimethoxyphenyl)ethyl]-2-iodobenzeneacetamide, mp 163°–164° C.
2-Iodo-5-methoxy-N-(2-phenylethyl)benzenepropanamide, mp 131°–132° C.
N-[2-(3,4-Dimethoxyphenyl)ethyl]-2-iodo-N-methyl-5-methylthiobenzenepropanamide (oil)
N-[2-(3,4-Dimethoxyphenyl)ethyl]-5-fluoro-2-iodo-N-methylbenzenepropanamide (oil)

EXAMPLE 10

N-[2-(3,4-dimethoxyphenyl)ethyl]-2-iodo-5-methoxy-N-methylbenzenepropanamine 4-Methylbenzene Sulfonate A slurry of N-[2-(3,4-dimethoxyphenyl)ethyl]-2-iodo-5-methoxy-N-methylbenzenepropanamide in 180 ml of THF was added over a 15-minute period to 126 ml (0.126 mole) of 1 M BH₃.THF solution under N₂. The mixture was heated to reflux for two hours. The reaction mixture was cooled in an ice/water bath and quenched by addition of a mixture of 25 ml of water and 25 ml THF. The solvents were evaporated in vacuo, the residue treated with 50 ml of propionic acid and heated to reflux for 1½ hours. After cooling to room temperature, the mixture was partitioned between 600 ml of water and 400 ml of ether. The pH was adjusted to pH 8 by addition of 50% sodium hydroxide solution. The aqueous phase was separated and further basified with sodium hydroxide to pH 12 followed by extraction with 200 ml of ether. The combined ether extracts were washed with two 500 ml portions of 10% sodium hydroxide solution and dried over anhydrous potassium carbonate. The solvent was removed in vacuo to yield a colorless oil. The oil was partially dissolved in methanol and the insoluble materials present removed by filtration through diatomaceous earth. The resulting clear solution was treated with p-toluenesulfonic acid until neutral and the solvent removed in vacuo. The resulting residue was treated with ethanol and evaporated in vacuo two times. The residue was then dissolved in 40 ml of hot ethanol and filtered through diatomaceous earth. The filtrate was treated with ether to the cloud point and the mixture allowed to crystallize at room temperature. The resulting crystals were filtered and washed with ether to yield 10.6 g (39%) of crude product. One recrystallization from ethanol/ether afforded pure N-[2-(3,4-dimethoxyphenyl)ethyl]-2-iodo-5-methoxy-N-methylbenzenepropanamine 4-methylbenzenesulfonate, a white solid, mp 105°–106.5° C.

EXAMPLE 11

Using the procedure of Example 10 and substituting equivalent quantities of the appropriate amide for N-[2-(3,4-dimethoxyphenyl)ethyl]-2-iodo-5-methoxy-N-methylbenzenepropanamide there were obtained as products:
N-[2-(3,4-Dimethoxyphenyl)ethyl]-2-iodo-5-methoxybenzeneethanamine (E)-2-butenedioate (1:1), mp 126°–131° C.;
2-Phenylethyl)-2-iodo-5-methoxybenzeneethanamine perchlorate, mp 178°–179° C.;
N-[2-(3,4-Dimethoxyphenyl)ethyl]-2-iodo-N-methyl-5-methylthiobenzenepropanamine oxalate, mp 132°–135° C.;
N-[2-(3,4-Dimethoxyphenyl)ethyl]-5-fluoro-2-iodo-N-methylbenzenepropanamine oxalate, mp 129°–131° C.

EXAMPLE 12

4-(3-Methoxyphenyl)-3-buten-2-one

A solution of 19.08 ml of 10% sodium hydroxide solution was added dropwise to a mixture of 103.6 g (0.761 mole) of 3-methoxybenzaldehyde, 117.2 g (2.02 mole) of acetone and 75 ml of water. The temperature was kept between 24° and 28° by intermittent application of cooling. After 2.75 hours the mixture was acidified with dilute hydrochloric acid and partitioned between CH$_2$Cl$_2$ and water. The organic layer was washed with water, dried with MgSO$_4$ and concentrated in vacuo to give 132.6 g of a yellow oil. The oil was distilled in a Kugelrohr at 0.5 Torr. A forerun, bp 90°–110° C., was taken and discarded. The main fraction was taken between 110° and 120° C. There was obtained 91.68 g (68% yield) of 4-(3-methoxyphenyl)-3-buten-2-one as a yellowish oil.

EXAMPLE 13

1-(3-methoxyphenyl)-1-octen-3-one

Following the procedure of Example 12 and substituting an equivalent quantity of 2-heptanone for acetone there was obtained 1-(3-methoxyphenyl)-1-octen-3-one, bp 110°–134° C., 0.3 mm/hg.

EXAMPLE 14

4-(3-Methoxyphenyl)-2-butanone

A solution of 30.1 g of 4-(3-methoxyphenyl)-3-buten-2-one in 200 ml of MeOH was hydrogenated over 200 mg of 10% palladium on carbon for two hours. The catalyst was filtered and the solvent evaporated in vacuo to give 30.2 g of yellow oily 4-(3-methoxyphenyl)-2-butanone.

EXAMPLE 15

1-(3-methoxyphenyl)octan-3-one

Following the procedure of Example 14 and substituting an equivalent quantity of 1-(3-methoxyphenyl)-1-octan-3-one for 4-(3-methoxyphenyl)-3-buten-2-one there was obtained as the product 1-(3-methoxyphenyl)octan-3-one as a colorless oil.

EXAMPLE 16

Ethyl 3-(2-bromophenyl)-2-methyloxiraneacetate

A 50 g (0.27 mole) sample of 2-bromobenzaldehyde was added to 33.3 g of dry potassium t-butoxide under N$_2$ at −78°. A 48.9 g (0.27 mole) sample of ethyl 2-bromopropionate was added slowly with stirring. The mixture was allowed to warm to room temperature and stir for 18 hr. The mixture was partitioned between ether and dilute HCl. The ether was washed with brine, dried (MgSO$_4$) and the solvent evaporated in vacuo. The residue was distilled under vacuum to give 53.2 g (69% yield) of ethyl 3-(2-bromophenyl)-2-methyloxiraneacetate as an oil, bp 110°–120° C., 0.005 mm/Hg.

EXAMPLE 17

2-Bromophenyl-2-propanone

A solution of 69.3 g (0.243 mole) of ethyl 3-(2-bromophenyl)-2-methyl oxiraneacetate in 100 ml of 95% ethanol was added to 9.72 g (0.243 moles) of sodium hydroxide. The solution was heated under reflux for 3 hr. The solvent was evaporated in vacuo. The residue was partitioned between ether and dilute HCl. The ether was washed with brine, dried (MgSO$_4$) and the solvent evaporated in vacuo to give 62.9 g of a yellow oil. The oil was heated at 240° in a kugelrohr to give 38.4 g of distillate. The material was distilled through a Vigreaux column to give 24.7 g (47% yield) of yellow oily 2-bromophenyl-2-propanone, mp 60°–65° (0.005 mm Hg).

EXAMPLE 18

N-[2-(3,4-Dimethoxyphenyl)ethyl]-2-iodo-5-methoxyalphamethybenzene ethanamine hydrochloride A mixture of 20.0 g (0.06 mole) of (2-iodo-5-methoxyphenyl)-2-propanone and 11.9 ml (0.07 mole of 3,4-dimethoxyphenylethylamine in 200 ml of chloroform was stirred overnight over 240 g of 5A molecular sieves. The solvent was evaporated in vacuo to give 26.39 of the corresponding imine. The imine was dissolved in 200 ml of methanol and 4 ml of methanolic hydrogen chloride and 2.91 g (0.046 mole) of sodium cyanoborohydride were added. The mixture was stirred for 3 days under an atmosphere of N$_2$. Additional methanolic hydrogen chloride was added over a several hour period to pH 1. The mixture was allowed to stand at room temperature overnight and the solvent evaporated in vacuo. The residue was partioned between ether and aqueous sodium hydroxide. The ether layer was washed with water and brine, dried (K$_2$CO$_3$) and evaporated in vacuo. The residue (24.5 g of an oil) was treated with ethereal hydrogen chloride to give the hydrochloride salt. It was recrystallized successively from 2-propanol and ethanol to afford N-[2-(3,4-dimethoxyphenyl)ethyl]-2-iodo-5-methoxyalphamethyl benzenethanamine hydrochloride, mp 170°–172° C.

EXAMPLE 19

Following the procedure of Example 18 and substituting 3,4-dichlorophenethylamine for 3,4-dimethoxyphenethylamine there was obtained as the product N-[2-(3,4-dichlorophenyl)ethyl]-2-iodo-5-methoxyalphamethylbenzenethanamine (E)-2-butenedioate (1:1), mp 91°–93° C.

EXAMPLE 20

2-Iodo-5-methoxy-N,alphadimethylbenzenepropanamine Hydrochloride

A solution of 19.41 g (0.625 mole) of methylamine in 400 ml of anhydrous methanol was treated with 37.92 g (0.125 mole) of 4-(2-iodo-5-methoxyphenyl)-2-butanone, 6.28 g (0.1 mole) of sodium cyanoborohydride and 21.07 g (0.312 mole) of methylamine hydrochloride and allowed to stir at room temperature under an atmosphere of nitrogen for 2½ hours. The resulting mixture was cooled in an ice bath and treated with concentrated hydrochloric acid to pH 1. The solvent was evaporated in vacuo and the residue partitioned between 1.5 l of water and 600 ml of ether. The water layer was separated and treated with 50% sodium hydroxide solution until basic. The resulting crude product was extracted into 500 ml of ether, washed with brine, and the brine layer extracted with an additional 400 ml portion of ether. The combined ether layers were dried over anhydrous potassium carbonate and evaporated in vacuo to yield 31.09 g (78%) of crude oil. The oil was dissolved in methanol and treated with ethereal hydrogen chloride until neutral. Ether was added to the mixture and the resulting hydrochloride salt separated by filtration to give 19.75 g (44%) of crude product. One recrystallization from 2-propanol yielded pure 2-iodo-5-methy-N-alphadimethylbenzenepropanamine hydrochloride a white solid, mp 189°–190° C.

EXAMPLE 21

2-Iodo-5-methoxy-N,alphadimethyl-N-[(phenyl)butyl]-benzeneethanamine

A solution of 3.5 g (12.1 mmole) of (2-iodo-5-methoxyphenyl)-2-propanone, 2.05 ml (12.7 mole) 4-phenylbutylamine and 23 mg (0.13 mmole) toluenesulfonic acid in 35 ml of toluene was heated under reflux for 45 minutes. The solvent was evaporated in vacuo. The residue was taken up in 18 ml MeOH and 0.85 g (1.6 mmole) of sodium cyanoborohydride and 0.13 ml of saturated ethereal hydrogen chloride were added. The mixture was stirred for 16 hours. To the mixture was added 2.45 ml (30.2 mmoles) of formalin and 3.69 g (44.8 mmole) sodium cyanoborohydride. The mixture was stirred 5 hours. It was acidified to pH 1 by the addition of concentrated HCl. The MeOH was evaporated in vacuo and the solution made basic with NaOH and extracted with $CH_2Cl_2$. The organic layer was washed with water, dried ($K_2CO_3$) and evaporated in vacuo to give 4.15 g of an oil. The oxalate salt was prepared from MeOH and recrystallized from 2-propanol/methanol to give 1.96 g (30% yield) of white crystaline 2-iodo-5-methoxy-N,alphadimethyl-N-[(phenyl)butyl]benzeneethanamine oxalate, mp 133°–135° C.

EXAMPLE 22

N-[3-(2-Iodo-5-methoxyphenyl)-1-methylpropyl]-3,4-dimethoxy-N-methylbenzeneacetamide A solution of 17.87 g (0.056 mole) of 2-iodo-5-methoxy-N, alphadimethylbenzenepropanamine in 58 ml of dry methylene chloride was added dropwise to a cooled (5° C.) solution of 3,4-dimethoxyphenylacetyl chloride in 68 ml of dry methylene chloride over a period of five minutes while stirring under an atmosphere of nitrogen. After about two minutes of stirring, 5.67 g (0.056 mole) of triethylamine was added followed by an additional 20 ml of dry methylene chloride. The reaction mixture was allowed to warm to room temperature while stirring overnight. An additional 80 ml of methylene chloride was added and the mixture washed successively with 200 ml of water, 300 ml of 5% hydrochloric acid, and 200 ml of sodium hydroxide solution. The organic phase was dried over anhydrous magnesium sulfate and evaporated in vacuo to yield 27.5 g (99%) of N- [3-(2-iodo-5-methoxyphenyl)-1-methylpropyl]-3,4-dimethoxy-N-methylbenzeneacetamide as an orange gum, MS (high resolution):

Calculated for M+1: 497.1063.
Found: 497.1057.

EXAMPLE 23

N-[2-(3,4-Dimethoxyphenyl)ethyl]-2-iodo-5-methoxy-N,alphadimethylbenzenepropanamine A solution of 27.19 g (0.055 mole) of N-[3-(2-iodo-5-methoxyphenyl)-1-methylpropyl]-3,4-dimethoxy-N-methylbenzeneacetamide was added dropwise over a 30 minute period with stirring to 165 ml of 1M $BH_3.THF$ under an atmosphere of nitrogen. The mixture was heated to reflux for 2.5 hours and then cooled to 0° C. in an ice bath. A mixture of 50 ml THF and 25 ml of water was added carefully and the resulting mixture was evaporated in vacuo to remove the THF. The residue was treated with 100 ml of water and 5.79 g of sodium hydroxide and heated to reflux for four hours. Heating was interrupted and an additional 10 g of sodium hydroxide was added. Heating was resumed for another hour. The mixture was cooled and extracted with two 300 ml portions of ether. The combined ether extracts were washed with water, brine, and dried over anhydrous potassium carbonate. The solvent was removed in vacuo to give 27.66 g of a yellow oil. The oil was partitioned between ether and 400 ml of 10% hydrochloric acid, at which time the resulting oil was separated, dissolved in a large volume of water, and washed with ether. The aqueous phase was treated with 10% sodium hydroxide solution until basic and extracted several times with ether. The combined ether layers were dried over anhydrous potassium carbonate and evaporated in vacuo to yield 20.98 g (79%) of a yellow oil.

The oil was converted to a crystalline oxalate salt from methanol, mp 189°–190° C. The oxalate salt was partitioned between methylene chloride and water and treated with a slight excess of sodium hydroxide. The methylene chloride layer was separated, dried over anhydrous potassium carbonate, and evaporated in vacuo to yield 16.33 g of N-[2-(3,4-dimethoxyphenyl)ethyl]-2-iodo-5-methoxy-N,alphadimethylbenzenepropanamine as a colorless oil.

EXAMPLE 24

1-Methoxy-3-(2-nitro-1-propenyl)benzene

A mixture of 71.9 g (0.528 mole) of m-anisaldehyde, 118.9 g (1.584 mole) of nitroethane, 40.7 g (0.528 mole) of ammonium acetate, and 350 ml of glacial acetic acid was heated to reflux for one hour. The mixture was then allowed to cool and partitioned between ether and water. The ether layer was separated and washed sequentially with water, 3N sodium hydroxide, water and brine. The organic phase was dried over anhydrous magnesium sulfate and evaporated in vacuo to give the crude product. After a preliminary distillation at 125° C./0.0001 mm, the product was finally crystallized from absolute ethanol to yield the pure product, a yellow solid, mp 40°–42° C.

EXAMPLE 25

3-Methoxy-α-methylbenzeneethaneamine

Two separate 3 liter three-necked round bottom flasks were each equipped with an overhead stirrer, condenser, addition funnel and nitrogen inlet tube. The flasks were purged with nitrogen and charged with 19.64 g (0.517 mole) of lithium aluminum hydride and 600 ml of anhydrous ether. To each flask was slowly added a solution of 25 g (0.129 mole) of 1-methoxy-3-(2-nitro-1-propenyl)benzene in 150 ml of anhydrous ether. An additional 500 ml of anhydrous ether was added to each flask, and the mixture allowed to stir overnight. After cooling in an ice bath, each reaction was treated cautiously and sequentially with 20 ml of water, 20 ml of 3N sodium hydroxide, and 60 ml of water, while maintaining cooling and stirring in the ice bath. Cooling and stirring were continued for 30 minutes, after which time the batch was removed and stirring continued until the inorganics formed a white solid. The inorganics were removed by filtration and washed with ether. The combined ether filtrates were washed with dilute sodium hydroxide, water, and brine. The ether layer was dried over anhydrous potassium carbonate and filtered. The filtrate was treated with ethereal hydrogen chloride to form the hydrochloride salt (mp 115°–118° C.) of the product, which was then converted back to yield 20.4 g of the free base, an oil.

EXAMPLE 26

1-(3,5-Dichlorophenyl)-3-methyl-1-butyn-3-ol

A mixture of 25.5 g (0.094 mole) of 3,5-dichloroiodobenzene, 550 ml dry triethylamine, 12 g (0.14 mole) of 2-methyl-2-hydroxy-3-butyne, 0.42 g (0.0019 mole) palladium (II) acetate, and 1 g (0.0038 mole) of triphenylphosphine was heated to reflux under nitrogen for four hours. The resulting mixture was cooled, diluted with ether and washed with two 500-ml portions of 3N hydrochloric acid. The ether layer was separated, dried over anhydrous magnesium sulfate, and evaporated in vacuo to yield the crude product as an oily residue. The purified product was obtained by distillation to yield 7.95 g, bp 115°–125° C./0.0001 mm.

EXAMPLE 27

1,3-Dichloro-5-ethynylbenzene

A mixture of 7.95 g (0.0655 mole) of 1-(3,5-dichlorophenyl)-3-methyl-1-butyn-3-ol and 30 g of sodium hydroxide in 150 ml of dry toluene was heated to reflux with stirring for 3.5 hours. The toluene was removed in vacuo to yield a brown solid residue. The residue was triturated with hexane and the resulting hexane solution washed with aqueous sodium thiosulfate solution. The hexane layer was separated and evaporated in vacuo to yield the crude product. Recrystallization from hexane yielded 4.15 g of pure product, mp 80°–81.5° C.

EXAMPLE 28

Copper I (3,5-Dichlorophenyl)acetylide

A mixture of 77 g of copper (II) sulfate pentahydrate and 30 ml of concentrated ammonium hydroxide was stirred under an atmosphere of nitrogen and 125 ml of water added. Stirring was continued until all of the copper sulfate dissolved, then 43 g of hydroxylamine hydrochloride was added with continued stirring for 30 minutes to form a pale blue solution. A solution of 4.15 g of 1,3-dichloro-5-ethynylbenzene in 150 ml of absolute ethanol was added dropwise with stirring to the pale blue copper solution. Stirring was continued an additional two hours, the mixture filtered and the resulting bright yellow product, a solid, washed sequentially with water, ethanol, and ether. The product was dried in vacuo to yield 4.25 g of copper (I) (3,5-dichlorophenyl)acetylide.

EXAMPLE 29

Using the procedures of Examples 26 and 27 substituting the appropriate Ar-iodide for 3,5-dichloroiodobenzene the following Ar-acetylenes were prepared respectively:

| Ar-iodide | Ar-acetylene | % Yield | bp 20 mm/Hg |
|---|---|---|---|
| 3-Iodotoluene | 3-Methylphenylacetylene | 88 | 90–110° |
| 4-Iodoanisole | 4-Methoxyphenylacetylene | 45 | 90° |
| 2-Iodothiophene | 2-Ethynylthiophene | 54 | 90–110° |

EXAMPLE 30

Using the procedure of Example 28 and employing equivalent quantities of the appropriate Ar-acetylene in place of 1,3-dichloro-5-ethynylbenzene the following copper (I) Ar-acetylides were obtained as bright yellow amorphous powders respectively:

| Ar-acetylene | Cu (I) Ar-acetylide | % Yield |
|---|---|---|
| 3-Methylphenylacetylene | Cu (I) 3-Methylphenylacetylide | 32 |
| 4-Methoxyphenylacetylene | Cu (I) 4-methoxyphenylacetylide | 70 |
| 2-Ethynylthiophene | Cu (I) 2-thienylacetylide | 9 |
| 4-Chlorophenylacetylene | Cu (I) 4-Chlorophenylacetylide | 88 |

EXAMPLE 31

N-[2-(3,4-Dimethoxyphenyl)ethyl]-5-methoxy-N-methyl-2 (phenylethynyl)benzenepropanamine Hydrochloride Hydrate (8:8:1)

A 100 ml round bottom flask was charged with a solution of 2.09 ml (19.0 mmole) of 98% phenylacetylene in 15 ml of dry THF. The solution was cooled to 0° C. and 11.62 ml (19.6 mmole) of n-butyllithium (1.6N in hexane) was added (solution turns from yellow to dark green). The mixture was allowed to stir for 15 minutes at 0° C. and transferred via cannula under argon to a flask containing 2.53 g (18.6 mmole) of anhydrous zinc chloride while maintaining a temperature of 0° C. The mixture was stirred for 15 minutes.

A solution of 7.27 g (15.5 mmole) of N-[2-(3,4-dimethyoxyphenyl) ethyl]-2-iodo-5-methoxy-N-methylbenzenepropanamine and 0.36 g (0.31 mmole) of tetrakis(triphenylphosphine) palladium in 100 ml THF was added to the reaction flask via cannula. The mixture was allowed to warm to room temperature and stir for 3½ hours. The reaction was quenched by addition of 20 ml of water and then partitioned between 500 ml of methylene chloride and 500 ml water. The organic phase was separated, washed with 500 ml of 5% hydrochloric acid, 500 ml of 5% sodium hydroxide, dried over anhydrous potassium carbonate, and evaporated in vacuo to yield an orange oil. The oil was dissolved in methanol and cooled in ice to form a yellow solid. The solid was removed by filtration and the filtrate evaporated in vacuo. The resulting residue was dissolved in ether and filtered through diatomaceous earth to remove some slight turbidity. The filtrate was evaporated in vacuo to yield an orange oil which was dissolved in methanol and treated with ethereal hydrogen chloride to pH 7.0 to 7.6. The solvent was removed in vacuo and the residue crystallized from t-butanol/ether with cooling. One recrystallization from t-butanol/ether afforded pure N-[2-(3,4-dimethoxyphenyl)ethyl]-5-methoxy-N-methyl-2-(phenylethynyl)benzenepropanamine hydrochloride hydrate (8:8:1), a white solid, mp 122°–123.5° C.

Anal Calc'd for $C_{29}H_{33}NO_3·HCl·\frac{1}{8}H_2O$: C, 72.22; H, 7.16; N, 2.90; $H_2O$, 0.47. Found: C, 71.84; H, 7.10; N, 2.89; $H_2O$, 0.29.

EXAMPLE 32

N-[2-(3,4-Dimethoxyphenyl)ethyl]-5-methoxy-N,alpha-dimethyl-2-[(phenyl)ethynyl] benzenepropanamine Hydrochloride.

A solution of 4.55 ml (41.4 mmole) of phenylacetylene in 40 ml of dry THF was cooled to 0° and 21.4 ml of 1.9M butyllithium in hexane (41.4 mmole) was added. The resulting solution was stirred for 15 minutes under $N_2$ then transferred to a flask containing 5.53 g (40.6 mmole) of dry $ZnCl_2$. The mixture was stirred 15 minutes at 0° and a solution of 16.33 g (33.8 mmole) of N-[2-(3,4dimethoxyphenyl)ethyl]-2-iodo-5-methoxy-N,alphadimethylbenzenepropanamine and 0.78 g (0.68 mmoles) of tetrakis(triphenylphosphine) palladium (0) in 100 ml of THF was added. The mixture was allowed to warm to room temperature and stirred for 24 hours. The mixture was diluted with $CH_2Cl_2$ and washed with water, 5% HCl, dilute NaOH, dried ($K_2CO_3$) and the solvent evaporated in vacuo. The residue was dissolved in MeOH and ethereal hydrogen chloride added. The solvent was evaporated in vacuo and the residue crystallized from 2-propanol/ether. The solid was recrystalled from 2-propanol/ether to give 5.53 g (33% yield) of N-[2-(3,4-dimethoxyphenyl)ethyl]-5-methoxy-N,alphadimethyl-2-(phenyl)ethynyl benzenepropanamine hydrochloride, mp 119°–122° C.

Anal. Calcd. for $C_{30}H_{35}NO \cdot HCl \cdot 0.5\ H_2O$: C, 71.62; H, 7.41; N, 2.78; $H_2O$, 1.79. Found: C, 71.65; H, 7.43; N, 2.70; $H_2O$, 1.45.

EXAMPLE 33

Using the procedure of example 32 and employing equivalent quantities of the appropriate iodoamine in place of N-[2-(3,4-dimethoxyphenyl)ethyl]2-iodo-5-methoxy-N-methylbenzenepropanamine, the following products were obtained respectively.

| Product | mp |
|---|---|
| N—[2-(3,4-Dimethoxyphenyl)ethyl]-5-methoxy-2-(phenylethynyl)benzeneethanamine Hydrochloride | 160–163 |
| 5-Methoxy-N—(2-phenylethyl)-2-(phenylethynyl)-benzenepropanamine (E)-2-Butenedioate (2:1) | 150–151 |
| N—[2-(3,4-Dimethoxyphenyl)ethyl]-5-methoxy-2-(phenylethynyl)benzenepropanamine (E)-2-Butenedioate | 151–153 |
| N—[2-(3,4-Dimethoxyphenyl)ethyl]-5-methoxy-alpha-methyl-2-(phenylethynyl)benzeneethanamine (E)-2-Butenedioate Hydrate (6:3:2) | 165–167 |
| N—[2-(3,4-Dimethoxyphenyl)ethyl]-5-methoxy-N—methyl-α-pentyl-2-phenylethynyl)benzenepropanamine Oxalate (1:1) | 131–133 |
| N—[2-(3,4-Dichlorophenyl)ethyl]-5-methoxyalpha methyl-2-[(phenyl)ethynyl]benzeneethanamine (E)-2-Butenedioate | 171–173 |
| N—[2-(3,4-Dimethoxyphenyl)ethyl]-5-fluoro-N—methyl-2-[(phenyl)ethynyl]benzenepropanamine Oxalate | 145–147 |
| N—[2-(3,4-Dimethoxyphenyl)ethyl]-N—methyl-5-methylthio-2-[(phenyl)ethynyl]benzenepropanamine Oxalate | 156–158 |

EXAMPLE 34

N-[2-(3,4-Dimethoxyphenyl)ethyl]-5-methoxy-2-[(4-methoxyphenyl)ethynyl]-N-methylbenzenepropanamine Ethanedioate (1:1)

A mixture of 3 g (6.4 mmole) of N-[2-(3,4-dimethoxyphenyl)ethyl]-2-iodo-5-methoxy-N-methylbenzenepropanamine, 1.5 g (7.7 mmole) of Copper (I) (4-methoxyphenyl)acetylide, and 75 ml of pyridine was heated overnight to reflux under an atmosphere of nitrogen. An additional 0.8 g of the copper compound was added and refluxing continued another four hours. The solvent was removed in vacuo and the residue partitioned between ether and concentrated ammonium hydroxide. The resulting solid was removed by filtration and the aqueous phase extracted with additional ether. The combined ether extracts were extracted with two portions of 3N hydrochloric acid. The acid extract was basified by addition of solid sodium hydroxide and extracted with ether. The ether layer was washed with water, brine and dried over anhydrous potassium carbonate. The ether was removed in vacuo and the residue partially purified by flash chromatography on silica using a 2:1 mixture of ethyl acetate:cyclohexane followed by HPLC purification on silica using a 9:1 mixture of ethyl acetate:cyclohexane. The oxalate salt was prepared by addition of one equivalent of oxalic acid in a mixture of 2-propanol and methanol. One recrystallization from 2-propanol afforded N-[2-(3,4-dimethoxyphenyl)ethyl]-methoxy-2-[(4-methoxyphenyl)ethynyl]-N-methylbenzenepropanamine ethanedioate (1:1), a white solid, mp 148°–150° C.

EXAMPLE 35

2-[(4-Chlorophenyl)ethynyl]-N-[2-(3,4-dimethoxyphenyl)ethyl]-5-methoxy-N-methylbenzenepropanamine (E)-2-Butenedioate Using the procedure of the foregoing example and substituting an equivalent quantity of Copper (I) (4-chlorophenyl)acetylide for copper (I) (4-methoxyphenyl)acetylide there was obtained as a white crystalline product 2-[(4-chlorophenyl)ethynyl]-N-[2-(3,4-dimethoxyphenyl)ethyl]-5-methoxy-N-methylbenzene propanamine (E)-2-butenedioate, mp 164°–166° C.

EXAMPLE 36

5-Methoxy-N,alphadimethyl-N-[(phenyl)butyl]-2-[(phenylethynYl]benzeneethanamine hydrochloride.

The free base of 2-iodo-5-methoxy-N,alphadimethyl-N-[(phenyl)butyl]benzeneethanamine hydrochloride (1.66 g, 3.1 mmole) was dissolved in 10 ml of triethylamine and 0.68 ml (6.2 mmole) of phenylacetylene, 11 mg (0.015 mmole) of bis(triphenylphosphine) palladium (II) chloride and 6 mg (0.03 mmole) copper (I) iodide were added. The mixture was stirred under argon at room temperature for 20 hours. An additional 6 mg copper (I) iodide and 11 mg bis(triphenylphosphine) palladium (II) chloride were added. The mixture was stirred for 20 hours. The solvent was evaporated in vacuo. The residue was taken up in $CH_2Cl_2$. The $CH_2Cl_2$ was washed with dilute HCl and dilute NaOH solution, dried ($K_2CO_3$) and the solvent evaported in vacuo. A hydrochloride salt was prepared from ethereal hydrogen chloride and recrystallized twice from 2-propanolether to give 0.46 g of 5-methoxy-N,alphadimethyl-N-[(phenyl)butyl]-2-[(phenyl)ethynyl]benzeneethanamine hydrochloride, mp 133°–135° C.

EXAMPLE 37

2-[(Phenyl)ethynyl]phenyl-2-propanone

A solution of 28.3 g (112 mmole) of 2-bromophenyl-2-propanone, 14.7 ml (134 mmole) of phenylacetylene, 1.8 g (2.24 mmole) of bis(triphenylphosphine) palladium (II) chloride and 0.85 g (4.48 mmole) of copper (I) iodide in 250 ml of triethylamine under nitrogen was heated under reflux for 3½ hours. An additional 3.6 ml of phenylacetylene, 0.36 g of palladium complex and 0.1 g copper (I) iodide were added. The mixture was heated under reflux for 3½ hours. An addtional 5.0 ml of phenylacetylene, 0.36 g of palladium complex and 0.17 g of copper (I) iodide were added. The mixture was heated under reflux for 2 hours. An additional 5.0 ml of phenylacetylene was added. The mixture was heated under reflux for 3½ hours. The solvent was evaporated in vacuo and the residue taken up in ether. The ether was washed with water and brine, dried ($K_2CO_3$) and the solvent evaporated in vacuo. The residue was flash chromatographed on silica gel with ethyl acetate:hexane, 9:1, as eluant. The solvent was evaporated from the major compound bearing fraction to afford 21.2 g (81% yeild) of 2-[(phenyl)ethynyl]phenyl-2-propanone as an oil.

EXAMPLE 38

[2-(5-Methoxyphenyl)ethynyl] phenyl-2-propanone

A solution of 5.5 g (18.9 mmole) 2-iodo-5-methoxyphenyl-2propanane (18.9 mmole), 4.15 ml (37.8 mmole) of phenylacetylene, 0.037 g cuprous iodide (1 mole percent) and 0.066 g of bis (triphenylphosphine) palladium (II) chloride (5 mole percent) in 60 ml of triethylamine was stirred for 18 hours under $N_2$ at room temperature. The mixture was partitioned between water and ether. The ether layer was washed succesively with cold hydrochloric acid solution, water and brine. It was dried over $MgSO_4$ and the solvent evaporated in vacuo to give 5.6 g (100% yield) of brown crystals. Recrystallization from methylcyclohexane afforded pure [2-(5-methoxyphenyl)ethynyl]phenyl-2-propanone, mp 60°-62° C.

EXAMPLE 39

N-[2-(3,4-Dimethoxyphenyl)ethyl]-5-methoxy-N-methyl-2-(phenylethynyl)benzeneethanamine (E)-2-Butenedioate A solution of 1.7 g (4.09 mmole) of N-[2-(3,4-dimethoxyphenyl)ethyl]-5-methoxy-2-(phenylethynyl)benzeneethanamine in 30 ml of methanol was treated with 0.85 ml (10.2 mmole) of 37% aqueous formaldehyde solution and 0.95 g (15.1 mmole) of sodium cyanoborohydride. The mixture was stirred under an atmosphere of nitrogen for six hours, methanolic hydrogen chloride was added to pH 1, and the mixture stirred overnight at room temperature. The solvent was evaporated in vacuo and the residue partitioned between 3N sodium hydroxide and ether. The organic phase was separated, washed with brine, dried over anhydrous potassium carbonate and evaporated in vacuo to yield crude free base of the product. The free base was combined with one equivalent of fumaric acid in 2-propanol and allowed to crystallize overnight with cooling. Filtering afforded 1.73 g of nearly pure product which was recrystallized from a mixture of 95% ethanol and 2-propanol to yield pure N-[2-(3,4-dimethoxyphenyl)ethyl]-5-methoxy-N-methyl-2-(phenylethynyl)benzeneethanamine (E)-2-butenedioate (1:1), mp 152.5°-154° C.

Anal. Calc'd. for: $C_{28}H_{31}NO_3 \cdot C_4H_4O_4$: C, 70.44; H, 6.47; N, 2.57. Found: C, 70.41; H, 6.48; N, 2.54.

EXAMPLE 40

By employing the appropriate starting materials and following the procedure of the foregoing example the following were prepared:

N-[2-(3,4-Dimethoxyphenyl)ethyl]-5-methoxy-N,α-dimethyl-2(phenylethynyl)benzeneethanamine (E)-2-Butenedioate (1:1), mp 124°-126° C.

N-[2-(3,4-Dichlorophenyl)ethyl]-5-methoxy-N,α-dimethyl-2(phenylethynyl)benzeneethanamine (E)-2-Butenedioate (1:1), mp 124°-127° C.

EXAMPLE 41

5-Methoxy-N-methyl-N-(2-phenylethyl)-2-(phenylethynyl)benzenepropanamine hydrochloride A mixture of 5.54 g (0.015 Mol) of 5-methoxy-N-(2-phenylethyl)-2-(phenylethynyl) benzenepropanamine, 1.34 g (0.0165 Mol) of 37% aqueous formaldehyde solution, and 2.16 g (0.045 mole) of 95-97% formic acid was heated on a steam bath for three hours until gas evolution ceased. The volatiles were removed in vacuo and the residue dissolved in water. Aqueous sodium hydroxide (1%) was added and the mixture extracted with two portions of ether. The combined ether extracts were washed with water and brine, dried over anhydrous potassium carbonate, and evaporated in vacuo to yield 4.92 g of yellow oil. The oil was dissolved in a minimum volume of methanol and neutralized with ethereal hydrogen chloride. Evaporation of the resulting solution yielded a vellow oil which crystallized from a mixture of t-butanol and ether to form white crystals. One recrystallization from t-butanolether gave pure 5-methoxy-N-methyl-N-(2-phenylethyl)-2(phenylethynyl)benzenepropanamine hydrochloride, a white solid, mp 111°-112° C.

Anal. Calc'd. for $Cz_7Hz_9NO \cdot HCl$: C, 77.21; H, 7.20; N, 3.34. Found: C, 77.23; H, 7.21; N, 3.35.

EXAMPLE 42

N-[2-(3,4-Dimethoxyphenyl)-1-methylethyl]-5-methoxy-alpha-methyl-2-phenylethynyl)benzeneethanamine (E)-2-Butenedioate (20:17)

A mixture 5.0 g (18.8 mmole) of 5-methoxy-2-methyl-2(phenylethynyl)benzeneethanamine, 3.3 ml (18.8 mmole) of 3,4-dimethoxyphenylacetone and 20 g of 5A molecular sieves in 45 ml of $CHCl_3$ was stirred at room temperature for 6 hours. An additional 0.3 ml of 3,4-dimethoxyphenylacetone and 20 g of molecular sieves were added and the mixture allowed to stand overnight. A third 20 g portion of molecular sieves was added and stirring resumed for 6 hours. The solids were removed by filtration and the filtrate evaporated in vacuo to give a yellow oil consisting of the corresponding imine.

The oil was dissolved in 50 ml of methanol and 0.72 g (11.4 mmole) of sodium cyanoborohydride and 1 ml of methanolic hydrogen chloride was added. The mixture was stirred at room temperature overnight. The pH was adjusted to pH 1 by the addition of methanolic hydrogen chloride and stirring was continued for 2 hours. The solvent was evaporated in vacuo and the residue was partioned between ether and 3 N sodium hydroxide solution. The organic phase was washed with water and brine and dried ($K_2CO_3$). The solvent was evaporated in vacuo to give an oil which was treated with one equivalent of fumaric acid in 2-propanol to give a crystalline salt which was recrystallized from 95% ethanol to give 1.54 g of N-[2-(3,4-dimethoxyphenyl)-1-methyl]-5-methoxy- alphamethyl-2-(phenylethynyl)benzeneethanamine (E)-2-butenedioate (20:17) as a white solid, mp 196°-199° C.

Anal. Calc'd. for $C_{29}H_{33}NO_3 \cdot 0.85 \, C_4H_4O_4$ C, 71.77; H, 6.77; N, 2.58. Found: C, 71.69; H, 6.86; N, 2.68.

EXAMPLE 43

N-[2-(3,4-Dimethoxyphenyl)ethyl]-alpha, N-dimethyl-2-(phenylethynyl)benzeneethanamine A mixture of 2.4 g (10.2 mmole) of 2-[(phenyl)ethynyl]- phenyl-2-propanone, 1.73 g (10.2 mmole) of homoveratrylamine and 35 g of 5A molecular sieves in 35 ml of chloroform was stirred overnight at room temperature under an atmosphere of nitrogen. The mixture was filtered and the sieves washed with chloroform. The filtrate was evaporated to yield 4.1 g (100%) of the corresponding imine.

The imine was dissolved in 40 ml of methanol and treated with 0.52 g (8.25 mmole) of sodium cyanoborohydride and allowed to stir overnight under an atmosphere of nitrogen. An additional 0.2 ml of homoveratryl amine and 2 ml of methanolic hydrogen chloride was added and stirring continued another 24 hours. A third portion of homoveratryl amine (0.4 ml) and 2 ml of methanolic hydrogen chloride was added and stirring resumed for another 24 hours. A 2.2 ml sample of 34% formaldehyde and 2.4 g of sodium cyanoborohydride were added. The mixture was stirred for three days, methanolic hydrogen chloride added to pH 1, and the mixture stirred for 30 minutes. The solvent was removed in vacuo and the residue dissolved in chloroform, washed with 12% sodium hydroxide solution, dried over anhydrous potassium carbonate and evaporated in vacuo to yield 4.3 g a dark oil. The crude product was partially purified by flash chromatography in silica gel by elution with acetone:methylene chloride. The fractions containing the desired product were evaporated in vacuo to yield 2.8 g of oily product. Further purification was accomplished by conversion to an oxalate salt in ethanol and regeneration of the free base to yield pure N-[2-(3,4-dimethoxyphenyl)ethyl]-alpha, N-dimethyl-2-(phenylethynyl)benzeneethanamine, an oil.

Anal. Calc'd. for $C_{28}H_{31}NO_2 \cdot \frac{1}{4}H_2O$: C, 80.44; H, 7.59; N, 3.35. Found: C, 80.55; H, 7.65; N, 3.29.

EXAMPLE 44

N-[(3,4-Dimethoxyphenyl)methyl]-5-methoxy-N,alpha-dimethyl-2-(phenylethynyl) benzeneethanamine hydrochloride To a solution of 3.12 g (11.8 mmole) of [2-(5-methoxyphenyl)ethynyl]phenyl-2-propanone and 1.96 ml (13.0 mmole) of 3,4-dimethoxybenzylamine in 40 ml of $CH_2Cl_2$ was added 22 g of 5A molecular sieves. The reaction was stirred for two days. The sieves were removed by filtration and the solvent was evaporated in vacuo. The residue was dissolved in 15 ml of MeOH and 0.75 g (9.4 mmole) sodium cyanoborohydride and 1 ml of saturated ethereal hydrogen chloride were added. The mixture was stirred for 3 days. A 22 ml (29.5 mmole) sample of formalin, 3.5 g (43.7 mmole) of sodium cyanoborohydride and 10 ml of MeOH were added. The mixture was stirred for 16 hours. The mixture was acidified to pH 1 by the addition of concentrated HCl and stirred until bubbling ceased. The reaction was partitioned between $CH_2Cl_2$ and water. The $CH_2Cl_2$ layer was washed with dilute NaOH solution and water, dried ($K_2CO_3$) and the solvent evaporated in vacuo to give 4.9 g of an oily residue.

An oxalate salt was prepared from 1.27 g oxalic acid in MeOH. The MeOH was evaporated in vacuo and the salt crystallized from 2-propanol/ether. There was obtained 2.5 g (28% yield of crystalline N-[(3,4-dimethoxyphenyl)methyl]-5-methoxy-N,alphadimethyl-2-[(phenyl)ethynyl]benzeneethanamine oxalate, mp 164°-166° C. The oxalate was converted to the free base by partitioning between $CH_2Cl_2$ and NaOH. The $CH_2Cl_2$ was evaporated in vacuo and the hydrochloride prepared from 2-propanol/ether. There was obtained 1.5 g of the hydrochloride salt, mp 181°'183.5° C.

EXAMPLE 45

Ethyl 3-aminobenzenepropanoate hydrochloride

A suspension of 100 g (0.52 moles) of 3-nitrocinnamic acid in 800 ml glacial acetic acid and 100 ml of methanol was hydrogenated at 50 pounds per square inch over 2.5 g 10% palladium on carbon until four equivalents of hydrogen were absorbed. The catalyst was filtered off, the filtrates combined and the solvent was concentrated in vacuo leaving a brown glass of 3-aminobenzenepropanoic acid. To this was added 1 liter of ethanolic hydrogen chloride which was heated to reflux for five hours. The solvent was evaporated in vacuo leaving a purple solid. Recrystallization from ethyl acetate yielded 88.0 g (74%) of ethyl 3-aminobenzenepropanoate hydrochloride, mp 132°-135° C.

EXAMPLE 46

Ethyl 5-amino-2-iodobenzenepropanoate hydrochloride

To a solution of 88.0 g (0.38 moles) ethyl 3-aminobenzenepropanoate in 380 ml glacial acetic acid was added 97.3 g (0.38 moles) iodine and 96.0 g (0.57 moles) silver acetate portionwise, alternating the additions beginning with the iodine. After two hours of stirring 10 g of iodine was added and stirring was continued for an additional hour. The reaction mixture was filtered and the solid washed well with acetic acid. The filtrate was extracted with chloroform. The chloroform layer was washed with sodium bisulfite solution then evaporated in vacuo. The resulting red oil was converted to the hydrochloric acid salt giving 118.3 g (72%) of ethyl 5-amino-2-iodobenzenepropanoate hydrochloride, mp 124°-127° C.

EXAMPLE 47

Sodium 2-iodo-5-methylthiobenzenepropanoate

A mixture of 30 g (0.089 moles) of ethyl 5-amino-2-iodobenzenepropanoate, 30 ml water, 20 g ice and 45 ml of hydrochloric acid was stirred for one hour. The solution was cooled to 0° C. and 5.8 g (0.084 moles) of sodium nitrite in 15 ml of water were added dropwise keeping the temperature below 5° C. After stirring for one hour the reaction mixture was added to a solution of 13.5 g (0.084 moles) of potassium ethyl xanthate in 20 ml of water. This was stirred for three hours. The reaction mixture was extracted several times with diethyl ether which was evaporated in vacuo. The resulting brown oil was taken up in 95% ethanol and 18.9 g (0.336 moles) of potassium hydroxide was added. After refluxing overnight under nitrogen the reaction was cooled. Methyl iodide (10.5 ml; 0.168 moles) was added and the reaction was stirred three more hours. The ethanol was evaporated in vacuo. The residue was partitioned between 3N hydrochloric acid and diethyl ether. The ether was washed with water, brine solution and dried over Mg $SO_4$. The ether was evaporated. Conversion to the sodium salt gave 14.3 g (49%) of sodium 2-iodo-5-methylthiobenzenepropanoate, mp 118°-122° C.

EXAMPLE 48

3-(5-Fluoro-2-iodophenyl)propionic acid

A mixture of 30 g (0.084 mole) of ethyl 3-(5-amino-2-iodophenyl) propionate 45 ml of concentrated hydrochloric acid, 25 ml of water, and 40 g of ice was stirred for 40 minutes then cooled to −10° C. A solution of 5.8 g of sodium nitrite in 20 ml of water was added dropwise with stirring while maintaining a temperature of −10° C. Stirring was continued for 1½ hours then 13 ml of 65% hexafluorophosphoric acid was added slowly and the mixture allowed to warm to room temperature and stirring for a period of one hour. The resulting solid as removed by filtration and wahed with water, 1:4:ethanol:water, and finally water. The solid was dried in vacuo, placed in 500 ml of xylene and heated at 130° for 2.5 hours, until gas evolution ceased. The solvent was removed in vacuo and the residue partially dissolved in ether. The insolubles were removed by filtration and the filtrate washed with sodium bicarbonate solution, 3N hydrochloric acid, water, and brine. The solvent was removed in vacuo to yield a brown oil which was purified by flash chromatography on silica using mixtures of ethyl acetate and hexane as the eluting solvent. The eluate was stripped in vacuo, the residue dissolved in ether, insolubles removed by filtration, and finally the solvent removed in vacuo to yield 9.3 g of nearly pure fluoro-iodo ester, a yellow oil.

The ester was dissolved in 100 ml of methanol and treated with 15.5 ml of 3N sodium hydroxide solution. The mixture was refluxed for three hours and the solvent removed in vacuo. The resulting residue was poured into 3N hydrochloric acid while cooling by addition of ice. The aqueous mixture was extracted with ether, the ether washed with brine and dried over anhydrous magnesium sulfate. The solvent was removed in vacuo to yield 8.9 g of 3-(5-fluoro-2-iodophenyl)propionic acid, a yellow oil.

EXAMPLE 49

N-[2-(3,4-Dimethoxyphenyl)ethyl]-5-methoxy-N,α-dimethyl-2-[4-(trifluoromethyl)phenylethynyl]benzeneethanamine (E)-2-Butenedioate (2:1)

To a deoxygenated solution of 5.0 g (10.6 mmole) of N-[2-(3,4-dimethoxyphenyl)ethyl]-2-iodo-5-methoxy-N,α-diethyl benzeneethanamine in 50 ml of triethylamine under Ar was added 0.25 g (0.21 mmole) of tetrakis(triphenylphosphine)palladium (0), 0.08 g (0.43 mmole) of CuI and 2.2 g (12.8 mmole) of p-trifluoromethylphenylacetylene. The reaction was heated under reflux for 16 hr. The mixture was cooled and filtered. Ether was added. The solvent was evaporated. The residue was taken up in MeOH and filtered. The solvent was evaporated. The residue was partitioned between water and ether. The ether layer was washed with brine, dried ($K_2CO_3$) and the solvent evaporated in vacuo. A 1.0 g sample of oxalic acid was added to the residue and the oxalate salt was recrystallized twice from 95% ethanol to give 2.8 of a solid. The oxalate salt was partitioned between $CH_2Cl_2$ and dilute NaOH solution. The organic solution was dried ($K_2CO_3$) and the solvent evaporated in vacuo. The residue was taken up in 2-propanol an 0.5 g of fumaric acid was added. There was obtained, after cllection of the precipatated salt by filtration, 1.97 g of the title compound as a white solid, mp 117.5°–119.5° C.

EXAMPLE 50

Using the procedure of Example 49 and substituting an equivalent quantity of the appropriately substituted phenylacetylene for p-trifluoromethylphenylacetylene, there were obtained as products repectively:

| | mp °C. |
|---|---|
| 4-[[2-[2-[[2-(3,4-Dimethoxyphenyl)ethyl]methylamino]propyl]-4-methoxyphenyl]ethynyl]benzonitrile E-2-Butenedioate (2:1) | 130–132 |
| 2-[[3,5-Bis(trifluoromethyl)phenyl]ethynyl]-N—[2-(3,4 dimethoxyphenyl)ethyl]-5-methoxy-N,α-dimethylbenzeneethanamine | yellow oil |
| N—[2-(3,4-Dimethoxyphenyl)ethyl]-5-methoxy-N,α-dimethyl-2-[[4-(methylthio)phenyl]ethynyl]benzeneethanamine hydrochloride | 93–95 |
| N—[2-(3,4-Dimethoxyphenyl)ethyl]-5-methoxy-N,α-dimethyl-2-[[4-(methylsulfinyl)phenyl]ethynyl]benzeneethanamine Hydrochloride (1:1) | 199–201 |
| N—[2-(3,4-Dimethoxyphenyl)ethyl]-2-[(4-fluoro phenyl)ethynyl]-5-methoxy-N,α-dimethylbenzene ethanamine (E)-2-Butenedioate (1:1) | 132.5–134 |
| N—[2-(3,4-Dimethoxyphenyl)ethyl]-5-methoxy-N,α-dimethyl-2-[[4-(dimethylamino)phenyl]ethynyl]-benzenethanamine | 99–100.5 |
| N—[2-(3,4-Dimethoxyphenyl)ethyl-5-methoxy-N,α-dimethyl-2-[[4-(1-methylethyl)phenyl ethynyl]benzeneethanamine | 55–6 |

EXAMPLE 51

Using the procedure of Example 21 and employing the appropriate amine in place of 4-phenylbutylamine and the appropriate ketone, (2-iodo-5-methoxyphenyl)-2-propanone or 4-(2-iodo-5-methoxyphenyl)-2-butanone there were obtained as products respectively:

| | mp °C. |
|---|---|
| N—[2-(3,4-Dichlorophenyl)ethyl]-2-iodo 5-methoxy-N,α-dimethyl-benzeneepropanamine p-toluenesulfonate | 160–162 |
| 2-Iodo-5-methoxy-N,α-dimethyl-N—[(3-phenyl)propyl]benzeneethanamine ethanedioate (1:1) | 133–135 |
| N—[(3,3-diphenyl)propyl]-2-iodo-5-methoxy-N,α-dimethylbenzeneethanamine | oil |

EXAMPLE 52

N-[2-(2,6-Dichlorophenyl)ethyl]-2-iodo 5-methoxy-α-methylbenzeneethanamine E-2-Butenedioate 1:1

A solution of 8.0 g (27.6 mmole) of 2-iodo-5-methoxyphenyl2 propanone, 5.5 g (29.0 mmole) of 2,6-dichlorophenyethylamine and 52 mg (0.28 mmole) p-toluenesulfonic acid in 100 ml toluene was heated under reflux with azeotropic removal of water. After four hours the solvent was evaporated in vacuo. The crude imine was dissolved in 100 ml MeOH and 1.4 g (22.1 mmole) of sodium cyanoborohydride was added. The mixture was stirred for 20 hr. A methanolic hydrogen chloride solution was added to bring the pH to 1. The mixture was stirred for 30 min. The solvent was evaporated in vacuo. The residue was partitioned between ether and 3N NaOH solution. The ether layer was washed with brine, dried and the solvent was evaporated in vacuo. The residue was combined with 3.0 g of fumaric acid in 2-propanol. The precipitated solid was collected to give 10.8 g of the title compound as a white solid, mp 172°–175° C.

EXAMPLE 53

Using the procedure of Example 52 and employing equivalent quantities of the appropriate amine in place of 2,6-dichlorophenethylamine and 2-iodo 5-methoxyphenyl-2-propanone or the appropriate ketone, there were obtained as products respectively:

|  | mp °C. |
|---|---|
| α-[[2-(2-Iodo-5-methoxyphenyl)-1-methylethyl]amino]-methylbenzenemethanol Hydrochloride | 162–168 |
| 2-Iodo-5-methoxy-α-methyl-N—[2-(4-nitrophenyl)-ethyl]benzeneethanamine E-2-Butenedioate | 150–160 |
| N—[2-(4-Chlorophenyl)ethyl]-2-iodo-5-methoxy-α-methylbenzeneethanamine |  |
| N—[2-(-Iodo-5-methoxyphenyl)-1-methylethyl]-2-naphthaleneethanamine ethanedioate | 167–169 |
| 2-Iodo-5-methoxy-N—(2-phenoxyethyl)-benzenepropanamine ethandioate | 167–169 |
| 2-Iodo-5-methoxy-α-methyl-N—(2-phenylethyl)-benzeneethanamine |  |
| N—[2-(2,6-Dichlorophenyl)ethyl]-2-iodo-5-methoxy-α-methylbenzenepropanamine |  |
| N—[2-(3,5-Dimethoxyphenyl)ethyl]-2-iodo-5-methoxy-α-methylbenzenepropanamine Hydrochloride | 133–136 |
| N—[2-(3,4-dimethoxyphenyl)ethyl]-5-(dimethylamino)-2-iodo-α-methylbenzenepropanamine ethanedioate | 138–142 |

EXAMPLE 54

N-[2-(3-Chlorophenyl)ethyl]-2-iodo-5-methoxy-α-Methylbenzeneethanamine Ethanedioate A solution of 30.0 g (0.10 mole) 2-iodo-5-methoxyphenyl-2-propanone, 16.1 g (0.10 mole) of m-chlorophenethylamine and 0.2 g (0.10 mmole) of p-toluenesulfonic acid in 200 ml of toluene was heated under reflux with azeotropic removal of water for 16 hr. The solvent was evaporated in vacuo. The residue (crude imine) was taken up in 100 ml of MeOH and 3.9 g (0.10 mole) of sodium borohydride pellets were added. After 3 hr an additional 0.89 g (0.023 mole) of sodium borohydride was added. The mixture was stirred for 16 hr. A 5 ml sample of glacial acetic acid was added. After bubbling ceased, the mixture was partitioned between $CH_2Cl_2$ and 3N NaOH solution. The organic layer was dried ($K_2CO_3$) and the solvent was evaporated in vacuo. The residue was combined with 10.1 g of oxalic acid in boiling MeOH. The solid was collected to give the title compound or a white crystalline solid, mp 194–197 (38 g, 87% yield).

EXAMPLE 55

Using the procedure of Example 54 and employing an equivalent quantity of the appropriate amine in place of m-chlorophenethylamine there were obtained as products respectively:

|  | mp °C. |
|---|---|
| 2-Iodo-5-methoxy-N—[2-(2-methoxyphenyl)ethyl]-α-methylbenzeneethanamine Ethanedioate | 167–169.5° C. |
| N—[2-(2,5-Dimethoxyphenyl)ethyl]-2-iodo-5-methoxy-α-methylbenzeneethanamine Ethanedioate | 115–117° C. |
| N—[2-(3,5-Dichlorophenyl)ethyl]-2-iodo-5-methoxy-α-methylbenzenethanamine (E)-2-butenedioate | 185–187° C. |

EXAMPLE 56

Using the procedure of Example 39 and employing the appropriate secondary amine from Examples 52 to 55 and formaldehyde or the appropriate aldehyde there were obtained as products respectively:

|  | mp °C. |
|---|---|
| N—Butyl-N—[2-(3,4-dimethoxyphenyl)ethyl]-2-iodo-5-methoxy-α-methylbenzeneethanamine |  |
| 2-Iodo-5-methoxy-N,α-dimethyl-N—[2-(phenyl)-ethyl]benzeneethamine Ethanedioate | 163–165 |
| N—[2-(2,6-Dichlorophenyl)ethyl]-2-iodo-5-methoxy N,α-dimethylbenzeneethanamine Perchlorate | 160–163 |
| N—[2-(2,6-Dichlorophenyl)ethyl]-2-iodo-5-methoxy N,α-dimethylbenzenepropanamine |  |
| N—[2-(3-Chlorophenyl)ethyl]-2-iodo-5-methoxy N,α-dimethylbenzeneethanamine Ethanedioate | 175–178 |
| N—[2-(2,5-Dimethoxyphenyl)ethyl]-2-iodo-5-methoxy-N,α-dimethylbenzeneethanamine Ethanedioate | 134–137 |
| N—[2-(3,4-Dimethoxyphenyl)ethyl-5-dimethylamino-2-iodo-N,α-dimethylbenzenepropanamine Ethanedioate | 172–173 |

EXAMPLE 57

Using the procedure of Example 49 and employing an equivalent quantity of the appropriate iodoamine from Examples 51–56 in place of N-[2-(3,4-dimethoxyphenyl)ethyl]-2-iodo-5-methoxy N,α-dimethylbenzeneethanamine and an equivalent quantity of phenylacetylene in place of p-trifluoromethylphenylacetylene there were obtained as products respectively:

|  | mp °C. |
|---|---|
| N—[3,3-(diphenyl)propyl]-2-methoxy-N,α-dimethyl-2-(phenylethynyl)benzeneethanamine (E)-2-Butenedionate | 160–162 |
| N—[2-(2,6-Dichlorophenyl)ethyl]-5-methoxy-α-methyl-2-(phenylethynyl)benzeneethanamine Hydrochloride | 169–171 |
| α-[[[2-[5-Methoxy-2-(phenylethynyl)phenyl]-1-methylethyl]amino]methyl]benzenemethanol (E)-2-Butenedioate (2:1) | 168–169 |
| N—Butyl-N—2-(3,4-dimethoxyphenyl)ethyl]-5-methoxy-α-methyl-2-(phenylethynyl)-benzeneethanamine | oil |
| N—[2-(3,4-Dimethoxyphenyl)ethyl]-5-(dimethylamino)-N,α-dimethyl-2-(phenylethynyl)benzenepropanamine Hydrochloride Hydrate (100:200:127) | 162–164 |
| 5-Methoxy-α-methyl-N—[2-(4-nitrophenyl)ethyl]-2-(phenylethynyl)benzeneethanamine (E)-2-Butenedioate (2:1) | 155–157 |
| N—2-(4-Chlorophenyl)ethyl]-5-methoxy-α-methyl-2-(phenylethynyl)benzeneethanamine (E)-2-Butenedioate Hydrate (100:75:14) | 162–164 |
| N—[2-[5-Methoxy-2-(phenylethynyl)phenyl]-1-methylethyl]-N—methyl-2-naphthaleneethanamine Hydrochloride Hydrate (25:25:9) | 135–137 |
| 5-Methoxy-α-methyl-N—(2-phenoxyethyl)-2-(phenylethynyl)benzenepropanamine (E)-2-Butenedioate (2:1) | 78–79 |
| N—[2-(2,6-Dichlorophenyl)ethyl-5-methoxy-α-methyl-2-(phenylethynyl)benzenepropanamine Hydrochloride | 156–159 |
| 5-Methoxy-N,α-dimethyl-N—(2-phenylethyl)-2-(phenylethynyl)benzeneethanamine Hydrochloride (1:1) | 150–151 |
| N—[2-(2,6-Dichlorophenyl)ethyl]-5-methoxy-N,α-dimethyl-2-(phenylethynyl)benzenepropanamine (E)-2-Butenadioate (1:1) | 131–134 |
| N—[2-(3-Chlorophenyl)ethyl]-5-methoxy-α-methyl-2-(phenylethynyl)benzeneethanamine Hydrochloride | 178–179 |
| N—[2-(2-Methoxyphenyl)ethyl]-5-methoxy-N,α-dimethyl-2-(phenylethynyl)benzeneethanamine Hydrochloride | 165–166 |
| N—[2-(3-Chlorophenyl)ethyl]-5-methoxy-N,α-dimethyl- | 83– |

-continued

| | mp °C. |
|---|---|
| 2-(phenylethynyl)benzeneethanamine Hydrochloride Hydrate (2:2:1) | 88 |
| N—[2-(2,5-Dimethoxyphenyl)ethyl]-5-methoxy-α-methyl-2-(phenylethynyl)benzeneethanamine Hydrochloride 2-Propanolate (4:4:1) | 143–145 |
| N—[2-(2,5-Dimethoxyphenyl)ethyl]-5-methoxy-N,α-dimethyl-2-(phenylethynyl)benzeneethanamine (E)-2-Butenedioate (1:1) | 138–140 |
| N—[2-(3,5-Dimethoxyphenyl)ethyl]-5-methoxy-α-methyl-2-(phenylethynyl)benzenepropanamine Hydrochloride | 144–146 |
| 2-[[2-(3,4-Dichlorophenyl)ethyl][2-[5-methoxy-2-(phenylethynyl)phenyl]-1-methylethyl]amino]ethanol Hydrochloride (1:1) | 113–115 |
| 5-Methoxy-α-methyl-N,N—bis (2-phenylethyl)-2-(phenylethynyl)benzenepropanamine Anal. Calc'd. for C$_{35}$H$_{37}$ NO: C 86.20; H, 7.65; N, 2.87 Found: C 86.07; H, 7.65; N, 2.72 | oil |
| N—[2-(3,5-Dichlorophenyl)ethyl]-5-methoxy-α-methyl-2-(phenylethynyl)benzeneethanamine (E)-2-Butenediate | 186–187 |
| N—[2-(3,5-Dichlorophenyl)ethyl]-5-methoxy N,α-dimethyl-2-(phenylethynyl)benzeneethanamine (E)-2-Butenedioate | |

EXAMPLE 58

Using the procedure of Example 36 and employing an equivalent quantity of the iodoamines from Example 51 in place of 2-iodo 5-methoxy-N,α-dimethyl-N-[4-(phenyl)butyl benzeneethanamine there were obtained as products, respectively:

| | mp °C. |
|---|---|
| N—[2-(3,4-Dichlorophenyl)ethyl]-5-methoxy-N,α-dimethyl-2-(phenylethynyl)benzenepropanamine Hydrochloride Hydrate (4:4:1) | 107–108 |
| 5-Methoxy-N,α-dimethyl-2-phenyl-ethynyl-N—[3-(phenyl)propyl]benzeneethanamine Hydrochloride | 204–205 |

EXAMPLE 59

N-[2-(3,5-Dimethoxyphenyl)ethyl]-5-methoxy-α-methyl-2-(phenylethynyl)benzeneethanamine (E)-2-Butenedioate 2:1

A 60 g sample of 5A molecular sieves was suspended in 100ml of toluene and 8.5 g (32 mmole) of 5-methoxy-2-(phenylethynyl)-2-propanone and 5.82 g (32 mmole) of 3.5-dimethoxyphenethylamine were added. The mixture was stirred for two days at room temperature. The sieves were filtered and washed with toluene. The solvent was evaporated in vacuo. The residue was taken up in 50 ml of MeOH and 0.4 g (10.6 mmole) of sodium borohydride (pellet) was added. After 90 min water was added. The mixture was partitioned between CH$_2$Cl$_2$ and water. The organic solution was washed with diluted hydrochloric acid. NaOH solution and water. The solution was dried (K$_2$CO$_3$) and the solvent water evaporated in vacuo. The residue was taken up in MeOH and 2.76 g fumaric acid added. The solid (9.14 g, 63% yield) was collected and dried to give the title compound as a white solid mp 185°–190° C. (decomposition).

EXAMPLE 60

Using the procedure of Example 59 and employing an equivalent quantity of the appropriate amine in place of 3,5-dimethoxyphenethylamine there were obtained as products respectively:

| | mp °C. |
|---|---|
| N—[2-(2-Chlorophenyl)ethyl]-5-methoxy-α-methyl-2-(phenylethynyl)benzeneethanamine Hydrochloride (1:1) | 158–159 |
| 5-Methoxy-N—[2-(3-trifluoromethylphenyl)ethyl]-α-methyl-2-(phenylethynyl)benzeneethanamine Hydrochloride (1:1) | 164–166 |
| 5-Methoxy-N—[2-(3-methoxyphenyl)ethyl]-α-methyl-2-(phenylethynyl)benzeneethanamine (E)-2-Butenedioate (2:1) | 154–156 |
| N—[2-(2,3-Dimethoxyphenyl)ethyl]-5-methoxy-α-methyl-2-(phenylethynyl)benzeneethanamine Hydrochloride | 162–163 |

EXAMPLE 61

Using the procedure of Example 39 and employing an equivalent quantity of the appropriate amine from Examples 57 and 59 in place of N-[3,4-dimethoxyphenyl)ethyl]-5-methoxy-N-methyl-2-(phenylethynyl)benzeneethanamine, there were obtained as products respectively:

| | mp °C. |
|---|---|
| 5-Methoxy-N—[2-(3-methoxyphenyl)ethyl]-N,α-dimethyl-2-(phenylethynyl)benzeneethanamine Hydrochloride (1:1) | 150–151 |
| N—2-(2,3-Dimethoxyphenyl)ethyl]-5-methoxy N,α-dimethyl-2-(phenylethynyl)benzeneethanamine (E)-2-Butenedioate (1:1) | 131–133 |
| N—[2-(3,5-Dimethoxyphenyl)ethyl]-5-methoxy-N,α-dimethyl-2-(phenylethynyl)benzeneethanamine Hydrochloride Hydrate (16:16:1) | 165–166 |
| N—[2-(2-Chlorophenyl)ethyl]-5-methoxy-N,α-dimethyl-2-(phenylethynyl)benzeneethanamine (E) 2-Butenedioate (1:1) | 136–139 |
| 5-Methoxy-N—[2-(3-trifluoromethylphenyl)ethyl]-N,α-dimethyl-2-(phenylethynyl)benzeneethanamine (E)-2-Butenedioate (1:1) | 130–132 |
| N—[2-(3,5-Dimethoxyphenyl)ethyl]-5-methoxy-N,α-dimethyl-2-(phenyethynyl)benzenepropanamine (E)-2-Butenedioate (1:1) | 127–129 |
| N—[2-(3,5-Dichlorophenyl)ethyl-5-methoxy-N,α-dimethyl-2-(phenylethynyl)benzeneethanamine (E)-2-Butenedioate (1:1) | 136–8 |

EXAMPLE 62

[[2-3,4-Dichlorophenyl)ethyl][2-[2-iodo-5-methoxyphenyl]-1-methylethyl]amine]ethanol (E)-2-Butenedioate A sample (1.3 g) of ethylene oxide was condensed in a pressure bottle at −68° and a cold solution of 4.2 g of N-[2-(3,4-dichlorophenyl)ethyl]-2-iodo-5-methoxy-α-methylbenzeneethanamine in 8 ml of MeOH was added. The bottle was sealed and heated on a steam bath overnight. A 1.0 g sample of fumaric acid was added. The solid was collected to give 3.3 g (60% yield) of the title compound as white crystals mp 138°–140° C.

EXAMPLE 63

4-(3-Dimethylaminophenyl)-3-butene-2-one

Using the procedure of Example 12 and employing an equivalent quantity of 3-dimethylaminobenzaldehyde in place of 3-methoxybenzaldehyde the title compound was obtained as a yellow solid, mp 47°–49° C.

EXAMPLE 64

4-(3-Dimethylaminophenyl)-2-butanone Ethanedioate

A 103 ml (0.38 mole) sample of tri-n-butyltin hydride was added dropwise over 15 min to a solution of 60.4 g (0.319 mole) of 4-(3-dimethylaminophenyl)-3-butene-2-one, 19.15 ml of glacial acetic acid and 3.7 g (0.032 mole) of tetrakis(triphenylphosphine)palladium (0) in 900 ml of dry toluene under $N_2$. The mixture was stirred for two hours, A 600 ml sample of 3N HCl was added and the mixture was stirred one hour. The acid layer was separated and the toluene layer was extracted three times with 3N HCl. The combined HCl solutions were made basic with NaOH solution. The mixture was extracted with ether. The ether was washed with brine and dried ($K_2CO_3$). The solvent was evaporated in vacuo. An oxalate salt was prepared from MeOH. There was obtained 67.5 g (75% yield) of the title compound as a solid mp 108°–110° C.

EXAMPLE 65

4-(5-Dimethylamino-2-iodophenyl)-2-butanone Hydrochloride

A solution of 0.16 moles of iodonium nitrate in 280 ml of $CHCl_3$ was added to 30.4 g of 4-(3-dimethylaminophenyl)-2-butanone. The mixture was stirred for 2 hr. Ether was added and the precipitated solid was removed by filtration. The solvent was evaporated in vacuo. The residue was partitioned between water and ether. The ether solution was washed with sodium thiosulfate solution and brine. The solution was dried ($K_2CO_3$) and the solvent evaporated. The residue was taken up in ether and ethereal hydrogen chloride added. The precipitate (47.4 g, 85% yield) of the title compound was collected mp 120°–121° C.

EXAMPLE 66

2-Iodo-5-methoxy-α-methvlbenzenepropanamine

A sample of 2.9 g (4.6 mmole) of sodium cyanoborohydride was added to a suspension of 50.7 g (0.66 mole) of ammonium acetate and 20.0 g (66 mmole) of 4-(2-iodo-5-methoxyphenyl)-2 butanone in 300 ml of MeOH. The mixture was stirred for 5.5 hr. Concentrated HCl solution was added to bring the pH to 1. The mixture was stirred for 16 hr. The MeOH was evaporated in vacuo, and the residue was partitioned between NaOH solution and ether. The organic solution was washed with brine, dried ($K_2CO_3$) and the solvent evaporated in vacuo to give 20.1 g of a vellow oil. The oil was combined with 7.64 g of furmaric acid in boiling 2-propanol. The solution was cooled and the crystals of title compound, were collected.

EXAMPLE 67

2-Iodo-5-methoxy-N,N-bis(2-phenylethyl)benzenepropanamine

A sample of 3.7 g (59 mmole) of sodium cyanoborohydride was added to a solution of 6.0 g (19.7 mmole) of 2 iodo-5-methoxy-α-methylbenzenepropanamine and 14.2 ml (0.12 mole) of phenylacetaldehyde in 60 ml of MeOH. Methanolic hydrogen chloride was added dropwise. After 16 hr the mixture was made frankly acidic by addition of methanolic hvdrogen chloride. The mixture was stirred for one hour. The MeOH was evaporated in vacuo and the residue partitioned between ether and NaOH solution. The ether was evaporated in vacuo. The residue was redissolved in ether and ethereal hydrogen chloride added. The ether was decanted from the precipitated gum and the gum washed twice with ether. The gum was partitioned between NaOH solution and ether. The ether was washed with brine, dried and the solvent evaporated in vacuo. The volatile by products were removed by heating the residue up to 125° C. at 0.005 mm Hg in a Kugelrohr. The pot residue contained 9.1 q 26% yield of the title compound as a pale yellow oil.

What is claimed is:

1. A pharmaceutical composition comprising N-[2-(3,4-dimethoxyphenyl)ethyl]-5-methoxy-N,alpha-dimethy-2-[(phenyl)ethynyl]benzenepropanamine or a pharmaceutically-acceptable, acid-addition salt in combination with a pharmaceutically-acceptable diluent or carrier.

2. A method of treating angina pectoris which compris administering to a mammal in need thereof the pharmaceutical composition of claim 1.

3. A method of treating hypertension which comprises administering to a mammal in need thereof the pharmaceutical composition of claim 1.

4. A pharmaceutical composition comprising N-[2-(3,5-dimethoxyphenyl)ethyl]-5-methoxy-α-methyl-2-(phenylethynyl)-benzeneethanamine or a pharmaceutically-acceptable, acid-addition salt thereof in combination with a pharmaceutically-acceptable diluent or carrier.

5. A method of treating angina pectoris which comprises administering to a mammal in need thereof the pharmaceutical composition of claim 4.

6. A method of treating hypertension which comprises administering to a mammal in need thereof the pharmaceutical composition of claim 4.

* * * * *